US011058286B2

(12) United States Patent
Ruppersberg et al.

(10) Patent No.: US 11,058,286 B2
(45) Date of Patent: Jul. 13, 2021

(54) EAR INSPECTION DEVICE AND METHOD OF DETERMINING A CONDITION OF A SUBJECT'S EAR

(71) Applicant: Helen of Troy Limited, Belleville (BB)

(72) Inventors: Peter Ruppersberg, Blonay (CH); Albrecht Lepple-Wienhues, Pontarlier (FR)

(73) Assignee: Helen of Troy Limited, St. Michael (BB)

( * ) Notice: Subject to any disclaimer, the term of this patent is extended or adjusted under 35 U.S.C. 154(b) by 916 days.

(21) Appl. No.: 14/762,438

(22) PCT Filed: Feb. 4, 2014

(86) PCT No.: PCT/EP2014/000295
§ 371 (c)(1),
(2) Date: Jul. 21, 2015

(87) PCT Pub. No.: WO2014/117956
PCT Pub. Date: Aug. 7, 2014

(65) Prior Publication Data
US 2015/0351637 A1 Dec. 10, 2015

Related U.S. Application Data

(60) Provisional application No. 61/809,048, filed on Apr. 5, 2013, provisional application No. 61/760,511, filed (Continued)

(30) Foreign Application Priority Data

Feb. 4, 2013 (EP) ..................... 13000552
Feb. 4, 2013 (EP) ..................... 13000553
Apr. 5, 2013 (EP) ..................... 13001748

(51) Int. Cl.
A61B 1/00 (2006.01)
A61B 1/05 (2006.01)
(Continued)

(52) U.S. Cl.
CPC ...... *A61B 1/00142* (2013.01); *A61B 1/00009* (2013.01); *A61B 1/00057* (2013.01);
(Continued)

(58) Field of Classification Search
CPC ............................. A61B 1/227; A61B 1/2275
See application file for complete search history.

(56) References Cited

U.S. PATENT DOCUMENTS 4,366,811 A 1/1983 Riester
4,380,998 A 4/1983 Kieffer, III et al.
(Continued)

FOREIGN PATENT DOCUMENTS

CN 1829468 A 9/2006
CN 102026574 A 4/2011
(Continued)

OTHER PUBLICATIONS

Wäny, M., et al., "Utrasmall Digital Image Sensor for Endoscopic Applications," in *Proc. of 2009 International Image Sensor Workshop*, Bergen, Norway, Jun. 22-28, 2009, 4 pages.
(Continued)

*Primary Examiner* — Jason M Ip
(74) *Attorney, Agent, or Firm* — Rankin, Hill & Clark LLP

(57) ABSTRACT

An ear inspection device configured for being at least partially introduced into an external ear canal for determining an ear condition, such as temperature, in particular at the subject's eardrum, wherein the device comprises an infrared sensor unit configured for detecting infrared radiation from the ear, and an electronic imaging unit configured for
(Continued)

capturing images based on radiation in the visible range from the ear, wherein the electronic imaging unit exhibits at least one optical axis arranged such that it can be radially offset within the ear canal, and wherein the infrared sensor unit exhibits a visual axis arranged such that it can be positioned centrically within the ear canal or radially offset within the same semicircle, especially the same quadrant, of the cross section of the ear canal.

39 Claims, 17 Drawing Sheets

Related U.S. Application Data on Feb. 4, 2013, provisional application No. 61/760,507, filed on Feb. 4, 2013.

(51) Int. Cl.

| | | |
|---|---|---|
| *A61B 1/227* | (2006.01) | |
| *A61B 5/01* | (2006.01) | |
| *A61B 5/107* | (2006.01) | |
| *A61B 5/11* | (2006.01) | |
| *A61B 1/06* | (2006.01) | |
| *A61B 1/07* | (2006.01) | |
| *A61B 5/00* | (2006.01) | |
| *A61B 5/06* | (2006.01) | |

(52) U.S. Cl.
CPC ...... *A61B 1/00066* (2013.01); *A61B 1/00101* (2013.01); *A61B 1/00179* (2013.01); *A61B 1/00193* (2013.01); *A61B 1/05* (2013.01); *A61B 1/051* (2013.01); *A61B 1/0623* (2013.01); *A61B 1/0638* (2013.01); *A61B 1/0676* (2013.01); *A61B 1/0684* (2013.01); *A61B 1/07* (2013.01); *A61B 1/227* (2013.01); *A61B 1/2275* (2013.01); *A61B 5/0075* (2013.01); *A61B 5/0086* (2013.01); *A61B 5/01* (2013.01); *A61B 5/1077* (2013.01); *A61B 5/11* (2013.01); *A61B 5/6817* (2013.01); *A61B 5/7203* (2013.01); *A61B 5/7221* (2013.01); *A61B 5/7246* (2013.01); *A61B 5/7264* (2013.01); *A61B 5/7275* (2013.01); *A61B 5/74* (2013.01); *A61B 5/065* (2013.01); *A61B 5/6885* (2013.01); *A61B 5/6886* (2013.01); *A61B 2562/0242* (2013.01)

(56) References Cited

U.S. PATENT DOCUMENTS

| | | | |
|---|---|---|---|
| 4,685,452 A | 8/1987 | Riester | |
| 4,766,886 A | 8/1988 | Juhn | |
| 5,280,378 A * | 1/1994 | Lombardo | ............ A61B 18/20 |
| | | | 359/199.1 |
| 5,363,839 A | 11/1994 | Lankford | |
| 5,445,157 A * | 8/1995 | Adachi | ................... A61B 1/05 |
| | | | 600/109 |
| 5,868,682 A | 2/1999 | Combs et al. | |
| 5,919,130 A | 7/1999 | Monroe et al. | |
| 5,935,058 A | 8/1999 | Makita et al. | |
| 5,951,486 A | 9/1999 | Jenkins et al. | |
| 6,093,150 A * | 7/2000 | Chandler | ................. A61B 8/12 |
| | | | 600/459 |
| 6,106,457 A * | 8/2000 | Perkins | .............. A61B 1/00041 |
| | | | 396/312 |
| 6,165,035 A | 12/2000 | Avner | |
| 6,319,199 B1 * | 11/2001 | Sheehan | ............ A61B 1/00055 |
| | | | 600/184 |
| 6,898,457 B1 | 5/2005 | Kraus et al. | |
| 7,529,577 B2 | 5/2009 | Jensen et al. | |
| 2002/0087084 A1 | 7/2002 | Shahar et al. | |
| 2002/0143257 A1 * | 10/2002 | Newman | ................... G01J 5/02 |
| | | | 600/474 |
| 2003/0108083 A1 | 6/2003 | Seitz | |
| 2003/0139672 A1 | 7/2003 | Cane et al. | |
| 2003/0164952 A1 * | 9/2003 | Deichmann | ............... A61B 1/05 |
| | | | 356/603 |
| 2004/0136010 A1 | 7/2004 | Jensen et al. | |
| 2005/0027168 A1 | 2/2005 | Strom et al. | |
| 2005/0192482 A1 | 9/2005 | Carpenter et al. | |
| 2005/0228231 A1 * | 10/2005 | MacKinnon | ............. A61B 1/05 |
| | | | 600/180 |
| 2006/0282009 A1 * | 12/2006 | Oberg | .................. A61B 5/0084 |
| | | | 600/559 |
| 2007/0112273 A1 | 5/2007 | Rogers | |
| 2008/0249369 A1 | 10/2008 | Seibel et al. | |
| 2009/0030295 A1 | 1/2009 | Shioi et al. | |
| 2009/0182526 A1 | 7/2009 | Quinn et al. | |
| 2009/0318758 A1 * | 12/2009 | Farr | ..................... A61B 1/0638 |
| | | | 600/112 |
| 2010/0060718 A1 | 3/2010 | Forster et al. | |
| 2011/0063428 A1 | 3/2011 | Sonnenschein et al. | |
| 2011/0112791 A1 * | 5/2011 | Pak | ........................ A61B 1/227 |
| | | | 702/131 |
| 2011/0137118 A1 | 6/2011 | Huang | |
| 2011/0257481 A1 | 10/2011 | Ogawa et al. | |
| 2012/0059224 A1 | 3/2012 | Wellen et al. | |
| 2012/0130168 A1 | 5/2012 | Konomura | |
| 2012/0179187 A1 | 7/2012 | Loushin et al. | |
| 2012/0253166 A1 | 10/2012 | Ahn et al. | |
| 2012/0327426 A1 | 12/2012 | Hart et al. | |
| 2013/0027515 A1 | 1/2013 | Vinther et al. | |
| 2013/0083823 A1 | 4/2013 | Harr et al. | |
| 2013/0237754 A1 | 9/2013 | Berglund et al. | |
| 2013/0289353 A1 * | 10/2013 | Seth | ....................... A61B 1/063 |
| | | | 600/200 |
| 2013/0296685 A1 | 11/2013 | Tsuboi et al. | |
| 2015/0351606 A1 | 12/2015 | Ruppersberg et al. | |
| 2015/0351607 A1 | 12/2015 | Ruppersberg et al. | |
| 2015/0351616 A1 | 12/2015 | Ruppersberg et al. | |
| 2015/0351620 A1 | 12/2015 | Ruppersberg et al. | |
| 2015/0374208 A1 | 12/2015 | Ruppersberg et al. | |

FOREIGN PATENT DOCUMENTS

| | | |
|---|---|---|
| EP | 0 472 490 A1 | 2/1992 |
| EP | 1 134 565 A1 | 9/2001 |
| EP | 1 477 107 A1 | 11/2004 |
| EP | 2 014 220 A1 | 1/2009 |
| EP | 2 277 439 A2 | 1/2011 |
| EP | 2 289 391 A1 | 3/2011 |
| JP | 63-40117 A | 2/1988 |
| JP | 5-253184 A | 10/1993 |
| JP | 7-111987 A | 5/1995 |
| JP | 9-19403 A | 1/1997 |
| JP | 11-28194 A | 2/1999 |
| JP | 11-113841 A | 4/1999 |
| JP | 11-316157 A | 11/1999 |
| JP | 2000-30063 A | 1/2000 |
| JP | 2001-517105 A | 10/2001 |
| JP | 2002-135887 A | 5/2002 |
| JP | 2002-528158 A | 9/2002 |
| JP | 2004-535834 A | 12/2004 |
| JP | 2005-519666 A | 7/2005 |
| JP | 2007-130084 A | 5/2007 |
| JP | 2007-144103 A | 6/2007 |
| JP | 2007-236734 A | 9/2007 |
| JP | 2009-153664 A | 7/2009 |
| JP | 2009-178482 A | 8/2009 |
| JP | 2009-201853 A | 9/2009 |
| JP | 2011-62370 A | 3/2011 |
| JP | 2011-72638 A | 4/2011 |
| JP | 2011-104333 A | 6/2011 |
| JP | 2011-520501 A | 7/2011 |
| JP | 2012-514200 A | 6/2012 |
| JP | 3178405 U | 8/2012 |
| JP | 2013-202260 A | 10/2013 |

(56) References Cited

FOREIGN PATENT DOCUMENTS

| | | | |
|---|---|---|---|
| JP | 2014-525774 A | 10/2014 | |
| JP | 2015-530886 A | 10/2015 | |
| KR | 10-2006-0122567 A | 11/2006 | |
| TW | 201225896 A1 | 7/2012 | |
| WO | 02/39874 A2 | 5/2002 | |
| WO | 2007/049562 A1 | 5/2007 | |
| WO | 2009/139548 A2 | 11/2009 | |
| WO | 2009/157825 A1 | 12/2009 | |
| WO | 2012/061697 A1 | 5/2012 | |
| WO | 2013/002935 A1 | 1/2013 | |
| WO | 2013/016651 A1 | 1/2013 | |

OTHER PUBLICATIONS

Wilke, M., et al., "Prospects and Limits in Wafer-Level-Packaging of Image Sensors," Electronic Components and Technology Conference (ECTC), 2011 IEEE 61st, Lake Buena Vista, Florida, May 31-Jun. 3, 2011, pp. 1901-1907.

Salvinelli et al., "The External Ear and the Tympanic Membrane: A Three-dimensional Study," *Scandinavian Audiology* 20(4):253-256, 1991. (5 pages).

\* cited by examiner

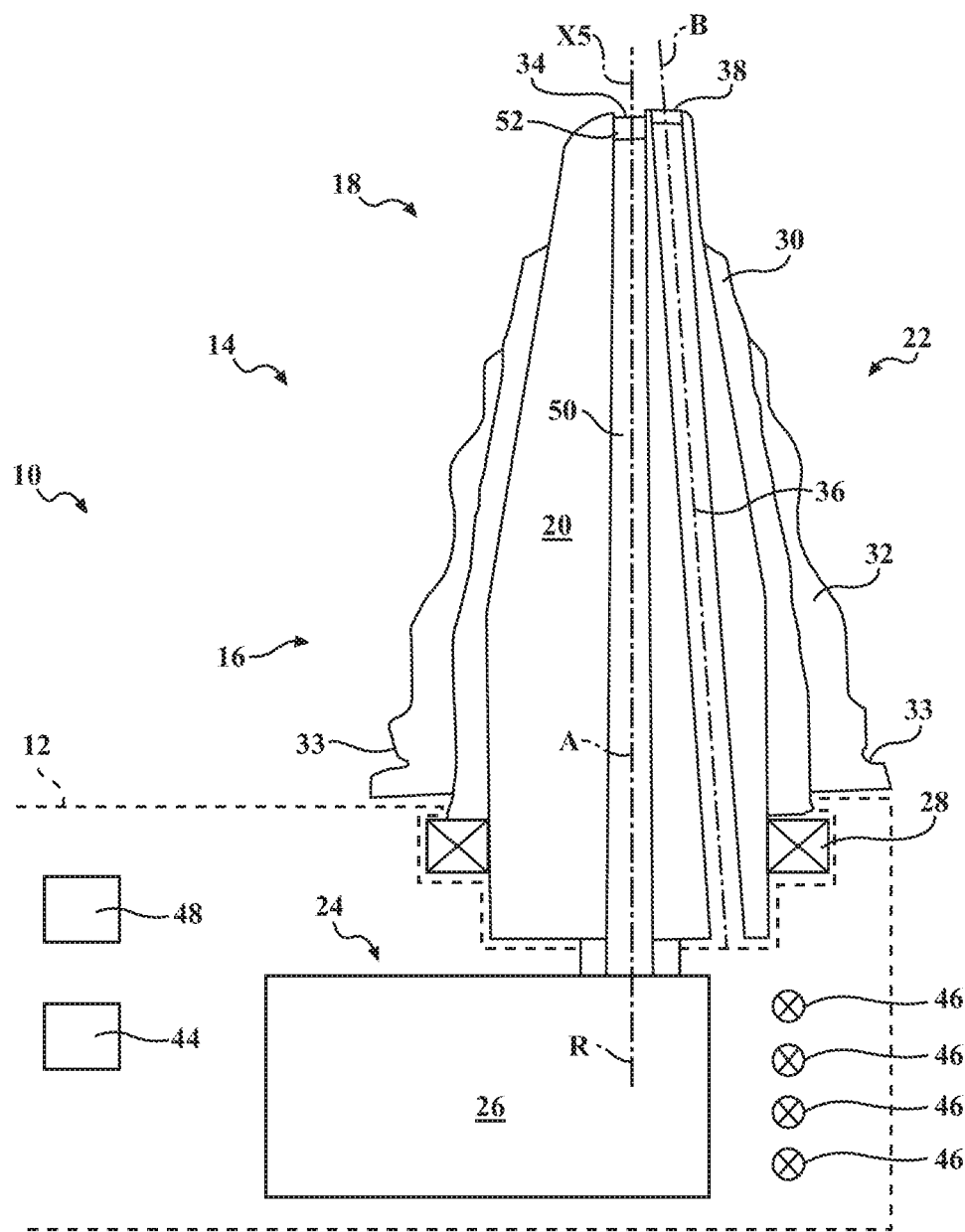
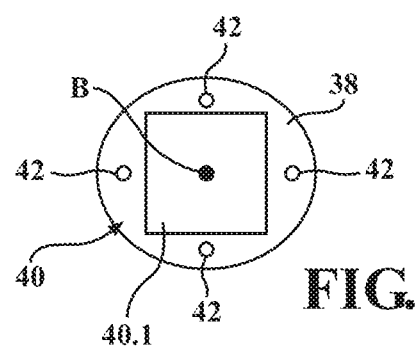
FIG. 1
FIG. 2

EAR INSPECTION DEVICE AND METHOD OF DETERMINING A CONDITION OF A SUBJECT'S EAR

FIELD OF THE INVENTION

According to one aspect, the invention refers to an ear inspection device configured for being at least partially introduced into a subject's external ear canal for determining a condition of the subject's ear, such as temperature, in particular at the subject's eardrum, wherein the ear inspection device comprises an infrared sensor unit configured for detecting infrared radiation from the subject's ear.

Such ear inspection devices are known e.g. as radiation thermometers, infrared thermometers or ear thermometers. A corresponding thermometer is disclosed, for example in the US patent document U.S. Pat. No. 6,898,457 B1 assigned to Braun GmbH. Such thermometers—not only used by physicians or other health care professionals but also by lay persons in the domestic field—have become more and more popular in recent years because the body core temperature can be determined very fast within only a few seconds with such a thermometer, and because measuring the temperature in the ear is generally more comfortable than measuring the temperature e.g. in the rectum with a classic mercury thermometer.

However, even though the existing infrared sensor units are capable of measuring temperatures of the surface of an object relatively precisely (i.e. to an accuracy of about $\frac{1}{10}°$ C.), the known ear thermometers, nevertheless, bear a risk of incorrect measurement of the subject's core temperature. The reason for this is that a free line of sight from the infrared sensor unit to the eardrum or tympanic membrane is mandatory for correctly measuring the subject's body core temperature. For example, if the device is oriented with respect to the subject's ear in such a way that the sensor is pointing to a surface of the exterior ear canal instead of to the eardrum, a too low temperature will be detected by the infrared sensor unit. The eardrum normally exhibits the highest temperature within the exterior ear canal, with the temperature of the eardrum substantially corresponding to the subject's body core temperature. For example, a normal temperature may be detected even when the subject has got high fever. Substantially the same is true if the ear canal is blocked by earwax, hair or dirt. In such a case, the infrared sensor unit will usually also detect a too low temperature (since there is no free line of sight to the eardrum). Obtaining unreliable or incorrect results for the body core temperature is critical, because a physician may thus make a wrong diagnosis and e.g. prescribe improper medicine to the subject.

Prior art document US 2013/083823 A1 describes an electronic thermometer with an infrared sensor unit and an electronic imaging unit, wherein the thermometer further includes a light source for illuminating the field of view of an image sensor.

Prior art document US 2009/182526 A1 describes an optically guided IR temperature measuring device including a microcomputer which is arranged to process both image light data and IR data.

Prior art document US 2011/112791 A1 describes a thermometer including a camera module with an image sensor and a display, wherein the camera module is provided at a distal end of the thermometer, and wherein the image sensor is arranged next to an IR temperature sensor and behind a lens and a light source.

Prior art document EP 1 134 565 A1 describes an imaging pyrometer with a specific type of image sensor, especially a CCD or CMOS. An infrared sensor can be provided in conjunction with the image sensor.

Prior art document U.S. Pat. No. 5,363,839 A describes a video otoscope with a compressible bulb which can be squeezed manually in order to exert a pressure within the ear canal and to move the tympanic membrane. The pneumatic bulb is attached to a head of the otoscope.

It is therefore the object of the present invention to provide an ear inspection device of the kind described above but being able to overcome the previously mentioned drawbacks of the prior art. In particular, it is an object of the present invention to provide an ear inspection device or a method that allows for reliable identification of objects in the subject's ear and that preferably shall be also domestically applied by laypersons without any—or at least with a significantly reduced—risk of causing injuries to the subject. In particular, it is an object of the present invention to provide an ear inspection device or a method of acquiring signals or data that allow for reliable differentiation of the eardrum, without the need of any assistance from a physician. The object of the present invention can also be describes as to provide an ear inspection device or a method that allows for reliable identification of the eardrum substantially irrespective of any specific medical experience or knowledge.

This object is achieved by the subject-matter of claim 1. The subject-matters of the dependent claims refer to preferred embodiments. In particular, this object is achieved by an ear inspection device configured for being at least partially introduced into a subject's external ear canal for determining a condition of the subject's ear, such as temperature, in particular at the subject's eardrum, wherein the ear inspection device comprises an infrared sensor unit configured for detecting infrared radiation from the subject's ear, and wherein—according to the present invention—the ear inspection device further comprises an optical electronic imaging unit configured for capturing images based on radiation in the visible range, i.e. visible light, from the subject's ear, wherein the electronic imaging unit exhibits at least one optical axis which is arranged such that it can be positioned radially offset within the ear canal, and wherein the infrared sensor unit exhibits a visual axis which is arranged such that it can be positioned centrically within the ear canal or radially offset within the same semicircle, especially the same quadrant, of the cross section of the ear canal.

Providing the ear inspection device known in the art additionally with an electronic imaging unit allows for verifying whether there is a free line of sight from the infrared sensor unit to the subject's eardrum or not and, therefore, whether the results obtained by the infrared sensor unit are reliable or not. The risk of misdiagnosis can thus be effectively minimized when using an ear thermometer for rapidly and comfortably measuring a subject's core body temperature.

The larger the radial offset, the better the view onto the eardrum, even in case the distal end is positioned only in a transition area between soft connective tissue and hard bone confining the ear canal. The electronic imaging unit may be arranged such that the radial offset is maximum with respect to the diameter of the distal end, in order to allow the otoscope for effectively looking around a curvature of the ear canal.

Providing a radially offset electronic imaging unit in conjunction with an infrared sensor unit which is arranged centrically or with a radial offset in the same radial direction or at least within the same semicircle of the distal tip allows for positioning both the imaging unit and the infrared sensor unit in a favorable observation point within the ear canal. This allows for evaluating acquired data of both the imaging unit and the infrared sensor unit, even in case the distal tip is not introduced deep into the ear canal.

Providing an infrared sensor unit in conjunction with a relatively small electronic imaging unit at the distal end of the head portion exhibiting at least one optical axis which is radially offset allows to "see" the patient's eardrum without the need to deform the patient's ear canal, or at least without having to deform the ear canal to such an extent as with the above described conventional otoscope. The reason for this is that there is no need for the "viewing direction" of the electronic imaging unit to correspond to the longitudinal axis of the head portion of the otoscope. Rather, the radial offset can ensure that there is a line of sight onto the eardrum even if the ear canal is not straightened, allowing the device to "look around the corner". In particular, in many cases, the ear canal of the outer ear is not straight-lined, but exhibits at least one curvature, especially at a transition area or transition point between soft connective tissue and hard bone confining the ear canal. The "corner" is provided by this curvature. In particular, virtually almost always, the ear canal has an S-shaped (sigmoid) form with a first curvature and a second curvature, the second curvature being closer to the eardrum than the first curvature. Particularly, the second curvature of the ear canal obstructs any optical line of sight or visual communication of an otoscope which is not introduced as far as at least some millimeters within the bony part of the ear canal. The "corner" can be defined as the second curvature of the ear canal. In particular, in a distal direction, the second curvature leads to the bony part of the ear canal. A transition point or area between soft connective tissue and hard bone is arranged at this second curvature. The second curvature leads into the section of the ear canal which is exclusively confined by hard bone. Preferably, the transition area can be defined as an area of about a few millimeters distal to (behind) and about a few millimeters proximal to (in front of) a curvature, especially 0 mm to 5 mm or 1 mm to 3 mm.

Preferably the electronic imaging unit captures images from the interior of the subject's external ear canal with a "main viewing direction" (or pointing direction), i.e. optical axis, of the electronic imaging unit substantially corresponding to the one of the infrared sensor unit. Alternatively the main viewing direction of the electronic imaging unit may be angled with respect to the main viewing direction of the infrared sensor unit. In the latter case, both main viewing directions preferably intersect at a point at which the subject's eardrum is supposed to be when the ear inspection device is properly introduced into the subject's exterior ear canal. The images are preferably captured by the electronic imaging unit simultaneously or substantially immediately before measuring the temperature by the infrared sensor unit.

Verification of the free line of sight may be performed "manually" by the operator of the ear inspection device, e.g. if the captured image is shown on a display unit provided either integrally with the ear inspection device Or separately thereof but operatively coupled thereto. Notably, the electronic imaging device may continuously capture images and provide these images to the operator in the form of a live video stream on the display unit. However, since such a "manual" verification can be prone to errors—especially when performed by lay persons—the verification may preferably be performed "automatically", e.g. by a logic unit capable of carrying out image recognition. With modern methods of image recognition it is possible to detect in a relatively reliable fashion whether the captured image shows the eardrum or not. Once at least one image has been captured by the electronic imaging unit, object recognition and unambiguous object identification (e.g. distinguishing objects, such as earwax, hair, and the eardrum) can be performed by determining brightness and/or color information of the pixels of the at least one captured image. Each pixel of the image obtained by the electronic imaging unit is characterized by a numerical value corresponding to the brightness of that pixel and—if the electronic imaging unit comprises a color camera—also by a numerical value corresponding to the color of that pixel. Different objects can thus be identified e.g. by their typical color and/or by brightness (when illuminated with a predetermined illumination source).

Usually, in pictures captured from the interior of a subject's ear, the eardrum is significantly darker than the wall of the exterior ear canal, usually showing a typical light reflex, when illuminated. In contrast to this, the captured image will show no particularly dark area when the exterior ear canal is blocked, e.g. with earwax. An optimum positioning or orientation of the ear inspection device with respect to the subject's ear may thus be obtained when the dark area (corresponding to the subject's eardrum) is substantially centered in the captured image.

The electronic imaging unit may comprise a video camera, preferably a wide angle video camera. The term "wide angle" in this context refers to angles of at least 80°, preferably of at least 110°, e.g. 120°. Such wide angle cameras allow detection of the subject's eardrum, even if the optical axis ("main viewing direction") of the camera is initially not directly centered to the eardrum. Once the eardrum has been detected in some region of the captured wide angle image, the operator of the ear inspection device may be informed, e.g. by some kind of guidance system, how to manipulate the position or orientation of the device with respect to the subject's ear so as to center the optical axis of the camera (and thus of the infrared sensor unit) to the eardrum. Preferably, a sequence of a plurality of images is captured by the electronic imaging unit, wherein only those data acquired by the infrared sensor unit may be taken into account that have been acquired with the optical axis of the camera substantially centered to the subject's eardrum. This allows reliably measuring the correct body core temperature. However, if it is not possible to detect the subject's eardrum in the image or images captured by the electronic imaging unit, a corresponding warning should be given to the operator of the ear inspection device. In such a case, a physician should be visited, e.g. because it may be necessary to clean the subject's external ear canal.

Notably, the term "infrared sensor unit" refers to all kinds of known and suitable infrared detectors as, for example, thermopiles, thermistors, bolometers, pyroelectric sensors, and semiconductor sensors.

Furthermore, the term "ear inspection device" is not limited to ear thermometers but refers to any kind of device for inspecting the subject's ear, in particular properties of the subject's eardrum. Thus, this term also refers to devices adapted for visual (otoscopic) inspection of the subject's ear, in particular the eardrum. Thus, the ear inspection device according to the present invention may be additionally or alternatively applied as video otoscope, wherein the electronic imaging device is preferably used to capture images of the interior of the subject's exterior ear canal.

When the ear inspection device according to the present invention is used as otoscope, there is a certain risk—especially if the operator is a lay person—that the images captured by the electronic imaging unit do not show the eardrum, but instead portions of the wall of the exterior ear canal and/or earwax, hair or dirt blocking the exterior ear canal and, thus, the free view on the eardrum. If the operator, e.g. a lay person, does not recognize that the image or images captured by the electronic imaging unit does/do not show the eardrum, he or she may conclude that there is probably no inflammation or infection of the eardrum and, therefore, that there is no need to consult a physician, even though this conclusion may be incorrect. To reduce this risk, the ear detection device according to the present invention preferably uses data measured by the infrared sensor unit to verify that the electronic imaging unit has a free line of sight to the subject's eardrum. As pointed out above, the main viewing direction of the electronic imaging device may substantially correspond to the one of the infrared sensor unit. Normally, the temperature at the surface of the eardrum (substantially corresponding to the subject's body core temperature) is higher than the temperature of the wall of the exterior ear canal and/or of earwax, hair or dirt in the exterior ear canal. Therefore, if the infrared sensor unit measures temperature values significantly (e.g. more than 2° C.) below the normal body core temperature of a human being, this represents a strong hint that the main viewing direction of the infrared sensor unit (and, thus, also of the electronic imaging device) is not directed to the eardrum and/or that there is no free line of sight to the eardrum. A corresponding warning may be emitted to the operator of the device.

As also mentioned above, the ear inspection device may comprise some kind of a guidance system for instructing the operator how to manipulate the position or orientation of the device with respect to the subject's ear so that the main viewing direction of the infrared sensor unit (and, thus, preferably also of the electronic imaging device) is directed to the area with the highest temperature within the subject's exterior ear canal. Such a guidance system reduces the risk of capturing images not showing the subject's eardrum when the device according to the present invention is used as an otoscopic device.

BACKGROUND OF THE INVENTION

For the above reasons, it is clear to those skilled in the art that the ear inspection device according to the present invention does not only provide the advantages of a known ear thermometer and of known (video) otoscopes, but that there additionally exists a strong synergetic effect of combining an infrared sensor unit and an electronic imaging unit within one device. That is, reliability of the data acquired by the infrared sensor unit or the electronic imaging unit can be significantly improved by the data acquired by the respective unit.

According to one embodiment, the ear inspection device is configured for positioning both an eccentric observation point arranged on the at least one optical axis and a temperature detection point arranged on the visual axis most distal within the ear canal with respect to a distal end of the ear inspection device. In other words: The ear inspection device is configured for introducing the electronic imaging unit as well as the infrared sensor unit as deep as possible, without the need of introducing the distal tip very deep. Such an ear inspection device allows for realizing large radial offset within the ear canal. In contrast, a radial offset of the optical axis or visual axis would not be effective in case the electronic imaging unit or the infrared sensor unit is not arranged most distal.

In order to benefit from this synergetic effect, the ear inspection device preferably further comprises a logic unit configured for receiving and processing signals (i.e. data) from the infrared sensor unit and the electronic imaging unit wherein the logic unit is configured for evaluating based on the signals if the at least one optical axis and/or the visual axis is in visual contact with the eardrum. The logic unit may be provided either integrally with the main portion of the ear inspection device or separately thereof—but operatively connected thereto. For example, the logic unit may form part of a remote device, such as a smart phone, having some kind of data connection with the remaining hardware of the ear inspection device.

It should be generally noted that the ear inspection device according to the present invention may comprise further features that are provided, for example, by modern digital photo cameras and known mobile phones. For example, the ear inspection device may comprise visual output means, such as a display, LEDs, etc., and/or acoustic output means, such as a loudspeaker, and/or a storage card slot for inserting a storage card to store the data acquired by the electronic imaging unit and/or the infrared sensor unit, and/or a cable connection port, such as an USB-port, and/or a wireless connection, such as Bluetooth®, WIFI®, and/or an energy supply, such as a battery.

Preferably, the logic unit is further configured for using the signals received from the electronic imaging unit and/or from the infrared sensor unit for verifying the correct positioning of the ear inspection device with respect to the subject's ear. As indicated above, such a verification process allows for enhancing reliability of the data acquired by the infrared sensor unit, or the electronic imaging unit by the data acquired by the respective unit. That is, either the image or images captured by the electronic imaging unit may be used to assure that the infrared sensor unit measures the temperature of the eardrum (i.e. the subject's body core temperature) or, vice versa, the temperature measured by the infrared sensor unit may be used to assure the correct "main viewing direction" and a free line of sight of the electronic imaging unit with respect to the subject's eardrum. Thus, it is possible to easily perform a plausibility check of the acquired data.

Additionally or alternatively, the logic unit may be further configured for determining—based on the received signals from the electronic imaging unit—whether the ear inspection device is positioned within the left or the right ear of the subject. To enable the device to distinguish between the left and the right ear has the following advantage: If an elevated temperature (i.e. a temperature above the normal body core temperature of a human being) is detected by the infrared sensor unit when the ear inspection device according to the present invention is introduced at least partially in one of the two exterior ear canals of the subject, this does not always allow to conclude that the subject has an elevated body core temperature, i.e. fever. Instead, the measured elevated temperature may result from a local inflammation of the eardrum of the ear into which the device has been introduced. Local inflammations also lead to a raise in temperature at the site of inflammation. To distinguish between these two cases, i.e. fever vs. local inflammation, it is advantageous to subsequently carry out the temperature measurement at both (i.e. left and right) ears of the subject. If the subject has got fever, the temperatures detected in both ears are supposed to be substantially the same, whereas, in the case that there is a local inflammation of an eardrum, the temperatures detected in both ears are supposed to differ significantly. Notably, it is rather unlikely that both eardrums are simultaneously inflamed—in particular inflamed to the same degree. In order to avoid any mistakes when subsequently performing several measurements of the temperature, it is advantageous if the device can automatically determine whether the temperature was measured within the left or the right ear of the subject. Only if at least one temperature signal from the left ear and at least one temperature signal from the right ear are available, the ear inspection device may compare the measured temperature signals so as to determine—and preferably inform the operator of the device—as to whether the subject has got fever and/or a local infection. If only measured temperature values from one ear, either the left or the right ear, are available, the device may inform the operator to carry out the measurement at the respective other ear of the subject.

Since there are specific differences in the aspects of the left exterior ear canal and the right exterior ear canal, modern image recognition methods are capable of relatively reliably distinguishing between images captured from the interior of the left ear and images captured from the interior of the right ear. In particular, the orientation of the malleus can be evaluated as an indicator for the left or right ear. An orientation in the direction of 11 o'clock may be evaluated as an indicator for the left ear, and an orientation in the direction of 1 o'clock for the right ear. Preferably, the orientation is evaluated with respect to the apical caudal axis, wherein during insertion of the head portion, the orientation of the outer ear may be determined.

Notably, the images captured by the electronic imaging unit may additionally be used to detect a local inflammation at the interior of a subject's ear by determining the spectral composition of reflections, especially the degree of reddishness, in the captured image.

In order to improve the identification of objects in the subject's ear, the logic unit is preferably further configured for identifying and discriminating different objects in the subject's ear, such as earwax, hair and the eardrum, by comparing their appearance in at least two images captured by the electronic imaging unit from different eccentric positions within the ear canal and/or with illumination from different positions within the ear canal.

The electronic imaging unit and preferably at least one light source may be introduced into an exterior ear canal of a subject; the electronic imaging unit may then be used to capture at least two images from different positions within the ear canal and/or with illumination from different positions within the ear canal; and the at least two captured images may be compared with each other to identify objects shown in the images.

In order to capture at least two images from different positions within the subject's exterior ear canal, the electronic imaging unit may be relocated when placed in the subject's ear canal and/or at least one further electronic imaging unit may be provided, wherein the two or more electronic imaging units are positioned at different sites in the ear canal. Alternatively or additionally, there may be provided at least one illumination unit which is adapted to illuminate objects within the ear canal from different positions (e.g. from two or more positions). Preferably, a combination of both approaches is realized by the inventive device, which allows capturing images from different positions under differing illumination conditions. Such a mode of action allows for reliable identification of distinct objects (e.g. the eardrum, particles of earwax, hair, etc. in the subject's ear), as will be described in more detail below. Thereby, the risk of image misinterpretation and failure in object recognition is significantly reduced.

If at least two images are captured from different positions within the ear canal, different objects, such as the eardrum and other objects, are discriminated by comparing their positions as provided in the at least two images. That is, it is possible to determine the distance of various objects in the ear canal with respect to the electronic imaging unit according to the fundamental principle of stereoscopic viewing, also known as "parallax". Parallax is a displacement or difference in the apparent position of an object viewed along two different lines of sight, and is measured by the angle or semi-angle of inclination between those two lines. For example, a person closing only his left eye sees objects being relatively close at a position other than by closing only his right eye. However, the person will see relatively remote objects substantially at the same position. The human brain is thus able to determine the distance from the observer to the objects as a result of the parallax phenomenon. The same approach may be realized by the logic unit of the ear inspection device according to the inventive method when capturing images from different positions within the ear canal. Since the electronic imaging unit will not and cannot be introduced too deeply into the subject's ear canal for not causing harm to the eardrum, the eardrum, as the membrane (object) terminating the ear canal, is relatively remote with respect to the electronic imaging unit, whereas other objects in the ear canal positioned more proximal to the electronic imaging unit are recognized as being less remote from the imaging unit as reference point. Thus, by the inventive method, e.g. the eardrum can be readily distinguished from other objects located more proximal in the ear canal.

Alternatively or additionally, different objects, such as earwax, hair, and the eardrum, within the subject's ear canal may be discriminated by comparing their appearance as depicted by at least two images captured under illumination from different positions (for each single image) within the ear canal. If an object positioned relatively closely to the electronic imaging unit, such as earwax, is illuminated from different positions within the ear canal (by e.g. two or more distinct light sources or by e.g. one single light source which can be repositioned), the appearance of such an object will significantly differ in the at least two captured images. Usually, the position of the sources of illumination is chosen such that they are still positioned closely to the electronic imaging unit. In contrast thereto, an object positioned relatively remote from the electronic imaging unit, such as the eardrum, will typically not change its appearance in the at least two captured images by such illumination from different positions.

If e.g. massive earwax blocking the subject's external ear canal has been detected by the logic unit as described above, the operator of the device may be informed correspondingly. In particular, he or she may be informed that a reliable temperature measurement is not possible (since there is no free line of sight between the infrared sensor unit and the eardrum). The subject may then go to see a doctor for having his or her ear professionally cleaned. Additionally and/or alternatively, the ear inspection device according to the present invention may comprise or may be combined with a flushing and/or suction unit in order to remove earwax based on the results of the earwax detection without the need to see the doctor. Corresponding flushing and/or suction units for cleaning ears are known in the art.

According to one embodiment, the ear inspection device is configured for evaluating the spectrum of reflected light, especially light reflected from the eardrum, especially in dependence on a specific intensity of illumination provided by the least one light source. The ear inspection device is configured for evaluating the spectrum of reflected light, especially light reflected from the eardrum, especially in dependence on a specific intensity of illumination provided by the least one light source. Evaluation of the spectral response can lead to more certain information with respect to the type of tissue observed and/or to a possible pathologic condition, e.g. an increased degree of reddishness in inflammation. Evaluation in dependence on the intensity can provide more reliable results, especially with respect to any characteristics of an inner lateral surface of the ear canal, facilitating to distinguish between the eardrum and an inner surface of the ear canal.

According to one embodiment, the ear inspection device is configured for varying an intensity of illumination provided by the at least one light source, especially during determination of the spectral composition of reflections. Thereby, the spectral composition of reflections, especially the degree of reddishness, may be determined based on at least two different intensities of illumination. Varying the intensity can provide more reliable results, especially with respect to any characteristics of the eardrum. In particular, the spectral composition of reflections can be determined with high accuracy. Preferably, the intensity is varied during the step of capturing a plurality of images, especially continuously varied. This allows for evaluating any change in the degree of reddishness more reliably, especially in conjunction with temperature detection. In particular, temperature detection and intensity variation are carried out with respect to the same are of interest or the same object, especially the eardrum. Varying the intensity can be carried out by a logic unit which is connected to a one light source or a plurality of light sources.

According to one embodiment, the ear inspection device is configured for adjusting the intensity of illumination with respect to specific areas of interest within the ear canal, especially in dependence on the type of object identified. In other words: During capture of at least one image or within a time period between capture of a first image and capture of a second image, the intensity of illumination is varied within a specific first range, e.g. in case an image of an inner lateral surface of the ear canal is captured, or the intensity of illumination is varied within a specific second range, e.g. in case an image of the eardrum is captured, the first range being different from the second range. Intensity variation is carried out with respect to specific areas of interest within the ear canal, such that feedback control of illumination intensity using areas of interest determined from the image sensor can be carried out. Images may be recorded at different illumination levels, each illumination level being optimized for evaluation of different areas of interest. In particular, a method according to the present invention may be carried out based on illumination levels being optimized for evaluation of the eardrum.

According to one embodiment, the ear inspection device is configured for adjusting an intensity of illumination provided by the at least one light source such that the subject's tympanic cavity arranged behind the eardrum can be identified, preferably such that light emitted by the at least one light source at least partially transilluminates the eardrum in such a way that it can be reflected at least partially by any object or fluid within the subject's tympanic cavity arranged behind the eardrum.

The intensity of illumination provided by the at least one light source is preferably adjusted in dependence on reflected radiation as received by the imaging unit, especially such that the subject's tympanic cavity arranged behind the eardrum can be illuminated through the eardrum and reflected light from the tympanic cavity can be observed and optimally illuminated respecting the dynamic range of the imaging sensor. Adjusting the intensity such that the background of the eardrum can be observed enables identification of the eardrum with higher reliability. Optimally illuminating the eardrum or its background while respecting the dynamic range of the electronic imaging unit facilitates reliable identification of the objects. Furthermore, pathological conditions in the middle ear, i.e. tympanic cavity, can be determined. The present invention is also based on the finding that identification of the tympanic cavity covered by a semitransparent membrane can facilitate identification of the eardrum, as the eardrum is the sole tissue within the outer ear canal which is arranged in front of a cavity. A feedback illumination control can be provided in conjunction with illuminating the eardrum, especially by a logic unit which is coupled with one or several imaging units and light sources.

The present invention is also based on the finding that information relating to characteristics of the patient's tympanic cavity can be evaluated or processed (e.g. by a logic unit) in order to provide the layperson with an advice as to whether a physician should be visited or not. In particular, the present invention is also based on the finding that any serous or mucous fluid within the tympanic cavity can be an indicator of the eardrum itself, and can be an indicator of a pathologic condition in the middle ear. Within the ear canal, only behind the eardrum, such body fluid can be identified. Thus, evidence of any body fluid can provide evidence of the eardrum itself, as well as evidence of a pathologic condition, e.g. OME.

In particular, the degree of reddishness or reflectivity of light in the red spectral range can be determined at different illumination intensities. It can therefore be distinguished more reliably between light reflected by the eardrum itself, or by objects or fluids behind the eardrum, or by the mucosal covering the tympanic cavity wall. The reflectivity of light may be evaluated with respect to reflectivity within e.g. the green or blue spectral range. Typical spectral wavelength maxima are 450 nm (blue light), 550 nm (green light), and 600 nm (red light) for a respective (color) channel. The electronic imaging unit, e.g. comprising a color video camera, or any color sensitive sensor, may record images with respect to the red, green or blue spectral range, respectively. A logic unit may calculate, compare and normalize brightness values for each read, green and blue image, especially with respect to each separate pixel of the respective image. Such an evaluation may also facilitate medical characterization of the eardrum. In particular, the healthy eardrum is a thin, semitransparent membrane containing only few relatively small blood vessels. In contrast, an inflamed eardrum may exhibit thickening and/or increased vascularization. Also, any skin or tissue confining the ear canal as well as any mucosa in the middle ear may be heavily vascularized. In other words: The reflectivity in the different spectral ranges varies considerably between the different structures or objects as well as between healthy and inflamed tissue. Thus, referring to the spectral range enables more reliable differentiation between light reflected by the eardrum itself, or by objects or any fluid behind the eardrum, or by the tympanic cavity wall covered by mucosa.

Thereby, the risk of confounding any red (inflamed) section of the ear canal and the eardrum can be minimized. Also, the eardrum can be identified indirectly by identifying the tympanic cavity. In particular, any opaque fluid, especially amber fluid containing leukocytes and proteins, within the tympanic cavity may influence the spectrum of reflected light, depending on the intensity of illumination. At a relatively high intensity of illumination, the spectrum of reflected light will be typical for scattering in serous or mucous fluid containing particles like leukocytes, as light transmits the eardrum and is at least partially reflected by the opaque fluid. At a relatively low intensity of illumination, the spectrum of reflected light will be dominated by the eardrum itself, as a considerable fraction of the light does not transmit the eardrum, but is directly reflected by the eardrum. Thus, information relating to the tympanic cavity, especially more detailed color information, can facilitate identification of the eardrum as well as of pathologic conditions in the middle ear.

In particular, the present invention is also based on the finding that transilluminating the eardrum can provide supplemental information with respect to the characteristics of the eardrum (e.g. the shape, especially a convexity of the eardrum), and/or with respect to the presence of any fluid within the tympanic cavity. Spectral patterns of reflected light which are typical for eardrum reflection and tympanic cavity reflection can be use to determine the area of interest as well as a physiologic or pathologic condition of the eardrum and the tympanic cavity, especially in conjunction with feedback controlled illumination.

The present invention is also based on the finding that any fluid within the tympanic cavity evokes a higher degree of reflection than the physiologically present air. The fluid increases reflectance. In contrast, in case the tympanic cavity is filled with air, any light transilluminating the eardrum is only reflected with inferior intensity, as most of the light is absorbed within the tympanic cavity. In other words: transilluminating the eardrum and evaluating reflected light in dependence on the intensity of illumination can facilitate determining specific characteristics of the eardrum, e.g. an absolute degree of reflectivity in dependence on different wavelengths and intensities, providing more information or more certain information with respect to the type of tissue and its condition. Evaluating reflected light can comprise spectral analysis of translucent reflection, especially at different illumination intensities.

The present invention is also based on the finding that the degree of reflection in the red spectrum from the area of the eardrum may depend on the illumination level, i.e. the intensity of illumination. In particular, the red channel reflection can increase with increasing intensity of illumination. The higher the intensity of illumination, the higher the red channel reflection intensity. Also, it has been found that at relatively high intensities of illumination, not only the eardrum, but also any other tissue will reflect more light in the red spectrum. Therefore, on the one hand, providing a control or logic unit which is arranged for adjusting the intensity of illumination can facilitate identification of the eardrum. On the other hand, it can facilitate determining specific characteristics of the eardrum, e.g. an absolute degree of red channel reflection, such that the red channel reflection provides more information or more certain information with respect to the type of tissue and state of the tissue.

In particular, the present invention is also based on the finding that the degree of red channel reflection does not increase in the same manner with increasing intensity of illumination, depending on the presence of body fluid behind the eardrum. It has been found that in case there is body fluid within the tympanic cavity, with increasing intensity of illumination, the degree of red channel reflection does not increase as strongly as if the tympanic cavity was empty. Thus, based on the (absolute) degree of red channel reflection, the presence of fluid behind the eardrum can be evaluated. This may facilitate determination of pathologic conditions, e.g. OME.

Varying or adjusting the intensity of illumination in conjunction with temperature measurement allows for reliable identification and characterization of objects within the ear canal.

The infrared sensor unit of the ear inspection device according to the present invention may comprise a plurality of infrared sensor elements for detecting infrared radiation from different regions of the ear. Such an infrared sensor is disclosed in the previously mentioned U.S. Pat. No. 6,898, 457 B1 assigned to Braun GmbH, the content of which is incorporated by reference herein. Preferably, only the temperature signal of the particular sensor element is used which supplies the peak temperature value by comparison with the remaining sensor elements. This peak temperature value most likely represents the temperature at the subject's eardrum since the eardrum usually exhibits the highest temperature within the subject's exterior ear canal.

More preferably, the infrared sensor unit of the ear inspection device according to the present invention may be formed by or may comprise an infrared camera configured for capturing images based on radiation in the infrared range from the subject's ear. This allows for obtaining a two-dimensional image of the temperature distribution in the area observed by the infrared camera.

The electronic imaging unit and/or the infrared camera may be a miniature camera, especially a wafer-level camera of a substantially flat configuration. Such wafer-level cameras may have dimensions of less than 3 mm×3 mm, preferably less than 2 mm×2 mm, even more preferably of about 1 mm×1 mm or even less than 1 mm×1 mm. Wafer-level cameras refer to a relatively new technology. They can be produced small in size with only about 3 microns per pixel. Therefore, wafer-level imaging technology allows obtaining images (of the temperature distribution and/or of light in the visual range) of "sufficient" resolution of the eardrum, e.g. images of 250 pixels×250 pixels, with a footprint of the camera (including a lens) of only about 1 mm×1 mm or even smaller.

Notably, existing wafer-level cameras usually comprise photo-sensitive elements already being sensitive to light in the infrared range (and not only to light in the visible range). However, the photo-sensitive elements of the existing wafer-level cameras are covered by filters. Usually one image pixel of the wafer-level camera is defined by four different photo-sensitive elements, one covered by a filter for allowing only red light to pass, one covered by a filter for allowing only green light to pass, one covered by a filter for allowing only blue light to pass, and a final one for determining the brightness. However, for a manufacturer of wafer-level cameras it is relatively easy to obtain a wafer-level camera sensitive to light in the infrared range by merely replacing at least one of the filters of the four photo-sensitive elements defining a pixel by a filter for allowing only infrared light to pass.

In order to reduce manufacturing costs of the inventive ear inspection device, the infrared sensor unit may be formed integrally with the electronic imaging unit. For example, the filters for allowing only blue light to pass may be replaced by filters for allowing only infrared light to pass. Even though such a design change of an existing waver-level camera does not allow for obtaining true-color images in the visible range from the subject's ear canal, for the purpose of the present device it may suffice to obtain images (in the visible range) only based on red and green colors. Alternatively, one may think about applying the four photo-sensitive elements of e.g. every second pixel of an existing waver-level with filters for allowing only infrared light to pass. Thus, the resolution (of images of visible light) of the waver-level camera would be reduced, e.g. to half. Moreover, it would be possible to further redesign an existing waver-level camera by providing five photo-sensitive elements per each image pixel of the camera, namely an additional photo-sensitive element having a filter for allowing only infrared light to pass.

Providing the infrared sensor unit integrally with the electronic imaging unit (i.e. providing both on the same chip) exhibits the further advantage that the main viewing direction of the infrared sensor unit will (automatically) coincide with the main viewing direction of the electronic imaging unit.

Advantageously, the ear inspection device of the present invention further comprises a mobility sensor unit adapted to detect reduced mobility of the eardrum, e.g. due to a reduced air pressure in the subject's middle ear. A mobility sensor unit represents a sensor unit for inspecting the mobility of the tympanic membrane. The mobility sensor unit allows for differentiation of the eardrum more reliably.

Immobilization of the eardrum can result either from fluid or from abnormal, especially low air pressure behind the eardrum. Therefore, the waves reflected from the eardrum will hardly be absorbed and/or attenuated by the eardrum. This can be determined e.g. by using an acoustic transducer and a microphone according to a technique known as "acoustic reflectance". This technique is described in detail in US patent document U.S. Pat. No. 5,868,682 B1, the content of which is also incorporated by reference herein. However, the technique of the mobility sensor unit may be based on any known technique, such as—but not limited to—acoustic reflectance, tympanometry and otoacoustic emissions.

The mobility sensor unit can be coupled with the electronic imaging unit or can be provided as a component of the electronic imaging unit, wherein the electronic imaging unit preferably is configured for inspecting the mobility of the subject's tympanic membrane when exposed to the varying pressure in the ear canal. Alternatively, according to one specific embodiment, the mobility sensor can be coupled with or can comprise optical means configured for inspecting the mobility of the subject's tympanic membrane when exposed to the varying pressure. This technique is also known as "pneumatic otoscopy", wherein this technique traditionally does not apply an electronic imaging unit but conventional optical means for visual inspection. According to the invention, the electronic imaging unit can be coupled with or can comprise such conventional optical means. According to one embodiment, the mobility sensor is provided separate from the electronic imaging unit. According to one specific embodiment, the mobility sensor as well as the optical means are provided separate from the electronic imaging unit.

Using the mobility sensor unit in conjunction with the electronic imaging unit for determining the mobility of the eardrum when subjected to varying pressure allows for omitting the usually applied optical means for visual inspection (such as multiple lenses), thereby achieving another synergetic effect. The mobility sensor unit may exhibit, e.g., a pressure sensor, especially in conjunction with an air pump (a manual or motorized air pump), in order to capture images at defined values of increased and/or decreased pressure within the ear canal. The air pump is arranged for subsequently decreasing and increasing the pressure within the ear canal. The change of appearance of the eardrum, as captured by the imaging unit, e.g. any changes within the reflections of the eardrum, or any change in shape, may be evaluated in order to assess the mobility of the eardrum.

For example, the mobility sensor unit may comprise pressurization means configured for applying a varying pressure within the subject's external ear canal or the otoscope is configured for being coupled with pressurization means and exhibits at least one gas conduit. The pressure is preferably applied by (compressed or evacuated) air, wherein an gas-tight chamber is formed by the subject's external ear canal and the corresponding device. Also, the mobility sensor unit may comprise or may be coupled with pressurization means configured for applying a varying pressure within the subject's external ear canal.

Another problem with otoscopes known in the art is that the ear has to be significantly deformed—which is uncomfortable or even causes pain to the subject—in order to have a direct view onto the eardrum. Furthermore, there is a risk of introducing the otoscope too far into the subject's interior ear canal thereby causing pain and injuries to the ear canal, and in particular to the eardrum. In order to better illustrate these problems reference to FIG. 5 is made in the following.

FIG. 5 shows a typical otoscope 10' as used for decades in otoscopy. The otoscope 10' comprises a handle portion 12' allowing the user to manipulate the otoscope during its application. The term "to manipulate" in this context refers to different kinds of manipulation, such as—but not limited to—holding the otoscope, aligning the otoscope with respect to the subject's ear, and turning on or off a light. The otoscope 10' further comprises a head portion 14' connected to the handle portion 12'. The head portion 14' exhibits a substantially tapering form—usually a conical form—extending along a longitudinal axis A' of the head portion 14'. The head portion 14' is substantially comprised of an empty funnel, wherein the tip of the funnel typically has a diameter of 3 mm. Furthermore, the head portion 14' has a proximal end 16' adjacent to the handle portion 12' and a smaller distal end 18' configured to be introduced in an ear canal C of a subject's outer ear. The term "end" in this context does not mean a single point but rather refers to a region or section of the head portion 14', wherein the proximal end 16' is located opposite to the distal end 18' with respect to the longitudinal axis A'. The ear canal C is partly surrounded by soft connective tissue C1 and—further down towards the middle ear—partly by hard bone C2.

The working principle of the known otoscope is typically to observe and simultaneously illuminate the subject's eardrum ED through the empty funnel with the 3 mm tip pushed deeply into the ear canal C. Normally, the eardrum ED is not visible from outside the ear, due to the natural curvature of the ear canal C. In order to overcome the natural curvature of the ear canal C, the skilled physician has to carefully pull the outer ear upward and to the back while carefully pushing the tip of the funnel as deeply as necessary to observe the eardrum. The ear canal C has to be deformed in such a way that the physician has a free view onto the eardrum ED along the optical axis of the otoscope 10', wherein the optical axis corresponds to the longitudinal axis A' of the head portion 14'. The optics of an otoscope is situated only at the wider end of the funnel at its proximal end 16' and essentially consists of a lamp and a lens (not shown) to magnify the image of the eardrum ED.

The otoscopy procedure thus needs manual skills and significant training to carefully push the funnel into the ear canal C while looking inside and manipulating the curvature of the ear canal C by pulling the ear. For example, it is very important for the trained physician to brace the hand holding the otoscope against the subject's head to avoid injury to the ear canal C by placing the index finger or little finger against the head. In particular in the case of young children—where the inner part of the ear canal is relatively short and sudden head movement during the examination may occur—there is a risk of penetration of the very sensitive ear canal skin or even of the eardrum ED. Besides pain and handicapped hearing, such an injury may even induce cardiovascular complications through a vagal overstimulation and therefore has to be avoided by all means.

Moreover, especially in an inflamed ear, the mechanical manipulation of "straightening" the ear canal C, especially by introducing the distal end far into the bony part of the ear canal, typically causes considerable discomfort or even pain, rendering the examination of an infant even more difficult.

FIG. 6 illustrates that with a distal tip of the otoscope 10' being positioned far within the bony part C2, the ear canal C has to be "straightened" considerably in such a way that the longitudinal axis A is directed onto the eardrum ED, at least approximately. The distal tip of the head portion 14' is supported within the bony part C2, such that a proximal end of the head portion 14' contacting the soft connective tissue C1 can push the soft connective tissue C1 downwards. The head portion 14' is shaped such that there remains the danger of touching the eardrum ED.

For the above reasons, reliable and secure handling of an otoscope of the art is currently subject to only well trained physicians and not amenable to the larger community of practitioners. A study recently published in the US as a result of a survey has shown that even physicians often fail to (correctly) determine the status of e.g. the subject's eardrum or fail to correctly interpret the image provided by the otoscope (i.e. correct and meaningful object recognition). Such failures result in misinterpretation of the status of the inner ear canal or the eardrum. As a consequence, e.g. over-medication with antibiotics for treating supposed inflammations of the eardrum occurs, because physicians tend to err on the side of caution, or meaningless image interpretation occurs.

Advantageously, the electronic imaging unit comprises at least one color video camera so as to allow determination of the color of the eardrum and/or of the inner portion of the subject's exterior ear canal. The electronic imaging unit may be configured for determining the spectral composition of reflections, especially the degree of reddishness, of the eardrum, once the eardrum has been identified. Thus the degree of reddishness of any physiological objects in the ear canal can be determined (skin of the ear canal or of the eardrum). Determining the spectral composition of reflections of e.g. the eardrum may help the lay person to decide as to whether a physician should be visited or not, as it usually indicates inflammation of the eardrum. Inflammation of the eardrum may suggest e.g. an (bacterial/viral) infection. Any such more advanced or final disease diagnosis has to be carried out by the physician on the basis of other symptoms exhibited by the subject, which are observed by the physician or by the physician's further examination. Notably, disease diagnosis should not exclusively be derived from the output provided by the ear inspection device according to the invention.

In view of these drawbacks of the known otoscopes, it is proposed that the ear inspection device according to the present invention further comprises a handle portion allowing a user to manipulate the ear inspection device during its application, and a head portion exhibiting a substantially tapering form extending along a longitudinal axis of the head portion, wherein the head portion has a proximal end adjacent to the handle portion and a smaller distal end configured to be introduced in the subject's external ear canal, and wherein the electronic imaging unit is positioned at the distal end of the head portion, especially at the distal tip, and wherein the electronic imaging unit exhibits at least one optical axis which is arranged radially offset from the longitudinal axis, wherein the infrared sensor unit exhibits a visual axis which is positioned centrically with respect to a distal tip or distal front side of the ear inspection device, especially on the longitudinal axis, or which is positioned radially offset from the longitudinal axis within the same semicircle, especially the same quadrant, of the distal tip or distal front side.

Providing a radially offset electronic imaging unit in conjunction with an infrared sensor unit which is arranged centrically or with a radial offset in the same radial direction or at least within the same semicircle of the distal tip allows for positioning both the imaging unit and the infrared sensor unit in a favorable observation point within the ear canal. This allows for evaluating acquired data of both the imaging unit and the infrared sensor unit, even in case the distal tip is not introduced deep into the ear canal.

By providing the preferably relatively small electronic imaging unit exhibiting at least one eccentric optical axis at the distal end of the head portion it becomes possible to "see" the subject's eardrum without the need to deform the subject's ear canal, or at least without having to deform the ear canal to such an extent as with the above described conventional otoscope. The reason for this is that there is no need for the "viewing direction" (corresponding to an optical axis) of the electronic imaging unit to correspond to the longitudinal axis of the head portion of the otoscope. Instead, the optical axis of the electronic imaging unit may be arranged at an angle with respect to the longitudinal axis, allowing the device to "look around the corner". In particular, in many cases, the ear canal of the outer ear is not straight-lined, but exhibits at least one curvature, especially at a transition area or transition point between soft connective tissue and hard bone confining the ear canal. The "corner" is provided by this curvature. An additional or alternative reason is that the field of vision of an electronic imaging unit provided at the distal end of the head portion can be much greater than the field of vision achievable with the relatively acute empty funnel of the otoscope according to the prior art.

Furthermore, in contrast to conventional otoscopes, the distal end of the head portion of the ear inspection device according to the present invention does not need to have a conical shape with a relatively thin open funnel, which shape bears the risk of introducing the distal end of the head portion too far into the ear canal, so as to cause serious injuries to the subject. Instead, the outer shape of the distal end of the head portion can be designed in such a way that it is practically impossible to introduce it too far into the ear canal. Thus, the otoscope according to the present invention can be securely and reliably operated even by lay persons without the risk of causing injuries to the subject. In particular, the otoscope according to the present invention allows for observing the ear drum substantially irrespective of the relative position of a head portion of the otoscope within the ear canal, especially irrespective of any specific insertion depth into the bony part of the ear canal, i.e. the section confined by hard bone.

In other words, the ear inspection device of the present invention allows for domestical inspection of a subject's ear by lay persons and medical doctors without extensive otoscopy training and without any—or at least with a significantly reduced—risk of causing injuries to the subject.

The electronic imaging unit and/or the infrared sensor unit may be positioned substantially centrically with respect to the longitudinal axis of the head portion. If the electronic imaging unit and/or the infrared sensor unit is/are positioned on the longitudinal axis of the head portion, the substantially flat electronic imaging unit and/or the infrared sensor unit is/are preferably inclined with respect of the longitudinal axis of the head portion, so that the optical axis (or the "main viewing direction") of the electronic imaging unit and/or the infrared sensor unit is/are angled with respect to the longitudinal axis of the head portion, allowing the ear inspection device to "look around the corner". Consequently, the ear inspection device according to the present invention does not have to be introduced as deeply into the subject's ear as in a conventional device of the prior art.

According to one embodiment, the radial offset of the at least one optical axis is at least factor 0.25 of the radial dimension of the distal end, preferably at least factor 0.3, more preferable at least factor 0.35. Such a relatively large radial offset can ensure positioning the optical axis in a favorable eccentric observation point within the ear canal, even in case the distal tip in introduced only as deep as a transition point between soft connective tissue and hard bone. Preferably, the distal end is configured for accommodating the electronic imaging unit and/or the infrared sensor unit in such a way that the radial offset of the at least one optical axis can be maximum with respect to the diameter of the distal end.

As described above, the electronic imaging unit and/or the infrared sensor unit may be positioned radially offset from the longitudinal axis of the head portion. A radially offset configuration also allows obtaining a free view onto the eardrum without having to introduce the electronic imaging unit and/or the infrared sensor unit as deeply as it would be necessary if the electronic imaging unit and/or the infrared sensor unit were placed just centrally on the longitudinal axis of the head portion. The offset may be at least 1 mm, preferably at least 2 mm, more preferably at least 3 mm from the longitudinal axis.

The head portion is preferably shaped in such a way that its distal end comprising the electronic imaging unit, and preferably also the infrared sensor unit, can be introduced only as deeply into the subject's ear canal as not to touch the eardrum. The ear canal of the subject's outer ear is limited by the eardrum. Notably, the ear canal of the subject's outer ear comprises an outer part which refers to a portion of the subject's outer ear (i.e. the subject's external auditory canal) that is surrounded by soft connective tissue and that usually comprises hair and earwax. The outer part comprises approximately the outer half of the ear canal of the subject's outer ear. Furthermore, the ear canal of the subject's outer ear also comprises an inner part which refers to a portion of the subject's outer ear (i.e. the subject's external auditory canal) that is surrounded by hard skull bone and that is usually free from any hair and earwax. This portion extends from the proximal end of the outer part of the ear canal of the subject's outer ear to the eardrum. The inner part of the ear canal is very sensitive to pain in case of mechanical friction. Injuring the inner part of the ear canal even bears the risk of cardiovascular complications through vagal overstimulation.

Preferably, a tip portion of the distal end can be introduced into the ear canal of the subject's outer ear no further than a few millimeters, preferably of at least 3 mm, from the eardrum, more preferable of at least 10 mm, further preferred of at least 15 mm.

As already mentioned above, the tapering head portion of the ear inspection device according to the present invention may be shaped with a blunt, rounded tip end, as compared to conventionally known devices, thereby reducing the risk of introducing injury or discomfort to the subject. Thus, the device can be securely handled by lay persons. The otoscope according to the present invention, nevertheless, allows detecting the eardrum, since the electronic imaging unit and/or the infrared sensor unit is/are provided at the distal end of the head portion.

Preferably, the distal end of the head portion is provided with a round and smooth shape. Moreover, the distal end may be made from a relatively soft material, such as silicone, or it may comprise an outer surface made of such a soft material. Furthermore, the longitudinal force upon introduction into the ear canal can be limited by a telescoping mechanism or the use of an elastic element.

When introducing the tip end of the head portion no deeper into the ear canal than to the border between the outer part and the inner part of the outer ear canal of the subject's outer ear, there is the risk that artifacts, such as earwax, hair and other kind of dirt from the outer part of the outer ear canal, obstruct the view of the small electronic imaging unit onto the eardrum. Therefore, as already mentioned above, it is advantageous to take several images from different positions within the ear canal. For doing so, the ear inspection device according to the present invention may comprise more than one electronic imaging unit at the distal end of its head portion, e.g. two imaging units, located at different positions on the head portion.

In another preferred embodiment, the electronic imaging unit comprises at least one miniature camera defining one of the at least one optical axis, and wherein both the at least one miniature camera and the infrared sensor unit are positioned at the distal tip of the head portion. Such an arrangement allows for effectively benefiting from a radial offset at the distal tip.

The infrared sensor unit may exhibit a field of vision with a wide angle, especially an angle of up to 150° or 160°, or even up to 180°. In contrast, the electronic imaging unit may exhibit a field of vision with a wide angle of (only) e.g. 120°. Thus, it is more advantageous positioning the infrared sensor unit centrically than positioning the electronic imaging unit centrically. Furthermore, the bony part of the ear canal as well as the eardrum radiate infrared radiation resulting from the body core temperature. Therefore, the orientation of the optical axis of the infrared sensor is less critical for a correct diagnosis than the orientation of the optical axis of the electronic imaging unit or its angle of the field of vision.

In another preferred embodiment, the electronic imaging unit comprises a plurality of miniature cameras, preferably three to six, especially four miniature cameras, each defining one of the at least one optical axis, wherein the infrared sensor unit is positioned substantially centrically with respect to the longitudinal axis and is surrounded, especially concentrically surrounded by the cameras. Providing miniature cameras concentrically around the infrared sensor unit enables to cope with the constricted space conditions at the tip, such that the infrared sensor unit can be positioned in an advantageous position. The electronic imaging unit may comprise wafer-level cameras of a substantially flat configuration, having dimensions of less than 3 mm×3 mm, preferably less than 2 mm×2 mm, especially 1.2 mm×1.2 mm, even more preferable of about 1 mm×1 mm or even less than 1 mm×1 mm. Dimensions of less than 2 mm×2 mm, even more preferable of about 1 mm×1 mm provide the advantage that the electronic imaging unit or cameras of the electronic imaging unit can be arranged very close to an outer lateral surface of the head portion, thereby enabling the otoscope to "look around the corner" with a relatively big angle, e.g. an angle in the range of 10° to 60°, preferably in the range of 15° to 40°, more preferable in the range of 20° to 30°. Preferably, the electronic imaging unit exhibits at least two optical axis which are arranged radially offset. A plurality of eccentric optical axis facilitates "looking around the corner". Alternatively, an optical component of beam splitter optics, such as a lens, can be provided radially offset.

According to one embodiment, the at least one optical axis is tilted against the longitudinal axis, wherein the visual axis of the infrared sensor unit substantially corresponds to the longitudinal axis. Such an arrangement provides for effectively "looking around the corner".

According to one embodiment, the electronic imaging unit exhibits beam splitter optics defining at least two optical axes which are arranged radially offset from the longitudinal axis. Beam splitter optics provide the advantage that the eardrum can be observed from different points of the distal tip of the head portion, without the need of a plurality of cameras or imaging sensors. With beam splitter optics, a relatively large radial offset of each optical axis can be realized, especially a radial offset which can be even larger than the radial offset of a camera or a relatively small miniature camera. In particular, optical components of the beam splitter optics, such as lenses, mirrors or prisms, can be provided with relatively small radial dimensions. In particular, the optical components can be provided with a radial dimension or diameter smaller than 1 mm, preferably smaller than 0.9 mm, even smaller than 0.8 mm or 0.7 mm.

Also, beam splitter optics can provide an aperture which exhibits relatively large radial dimensions. A large aperture provides for good optical characteristics, especially good light sensitivity and/or a high dynamic range. Also, beam splitter optics can provide an arrangement for "looking around the corner" which is cost-effective.

According to one embodiment, the at least one miniature camera and/or the infrared sensor unit are positioned at a distance of less than 3 mm, preferably less than 2 mm, more preferable less than 1 mm, from the distal tip. Such an arrangement, especially as close as possible to the distal tip, allows for providing the maximum eccentricity within the ear canal, allowing for effectively "looking around the corner".

In another preferred embodiment, the ear inspection device according to the present invention further comprises a motion mechanism configured to allow displacement of the electronic imaging unit and/or the infrared sensor unit relative to the handle portion. With such a motion mechanism, it is possible to capture a plurality of images or to acquire a plurality of temperature signals from different positions by one single electronic imaging unit and/or one single infrared sensor unit within the subject's ear canal, thereby avoiding the need for two or more electronic imaging units and/or infrared sensor units. If, for example, a hair at least partially obstructs the view of the electronic imaging unit and/or the infrared sensor unit at a certain position within the ear canal onto the eardrum, the electronic imaging unit and/or the infrared sensor unit may have a free view onto the eardrum at another position in the ear canal or may at least have a free view onto the part of the eardrum that was partially obstructed by the one hair before.

Moreover, providing such a motion mechanism also allows for automatic identification of different objects in the subject's ear according to the principle of stereoscopic viewing, as explained in more detail above.

The motion mechanism is preferably configured to allow at least partial rotation of the electronic imaging unit and/or the infrared sensor unit about an axis of rotation. The axis of rotation may correspond to the longitudinal axis of the head portion. By displacing the electronic imaging unit along a predefined motion path, it is possible to automatically calculate the distance between the electronic imaging unit and the detected objects, as described above. In view of the typical size of the artifacts found in the ear canal, such as hair and earwax particles, the motion mechanism preferably allows for displacement of the electronic imaging unit and/or the infrared sensor unit of at least 1 mm within the subject's ear canal. A rotation of at least 90°, more preferably of at least 120°, even more preferably of 180° or even more degrees around the axis may be realized. Preferably, the motion mechanism allows for rotation in both directions, i.e. clockwise and counter-clockwise. The motion mechanism may also allow for rotational displacement about more than one axis. The motion mechanism may comprise at least one motor and one or more gears and/or bearings. The electronic imaging unit and/or the infrared sensor unit may be connected to a flexible cable, e.g. a flexible ribbon cable, to allow for such a movement.

Preferably, the at least one optical axis and/or the infrared sensor unit is/are tilted against the axis of rotation so as to be continuously directed to a predetermined point on the axis of rotation, the predetermined point having a fixed distance to the electronic imaging unit and/or the infrared sensor unit. In view of the typical length of the inner part of the outer ear canal of the subject's outer ear, the distance may be between 3 mm and 20 mm. Thus, an optical axis (corresponding to a "viewing direction") of the electronic imaging unit and/or the infrared sensor unit is optimized for centering on the eardrum, which usually represents the object of primary interest within the subject's ear.

For hygienic reasons, the ear inspection device preferably further comprises an at least partially transparent (preferably to both, visual and infrared light) probe cover configured to be put over the head portion. The probe cover may be made from a plastic material, preferably from a transparent plastic material. Such a probe cover may be designed as a single-use product that can be produced in large numbers with low costs. The probe cover shall be transparent, at least at the locations where it covers the electronic imaging unit and/or the infrared sensor unit, so as to allow the electronic imaging unit and/or the infrared sensor unit to have a clear view onto the eardrum. The probe cover also inhibits contamination of the head portion of the ear inspection device, in particular when introducing the head portion into the subject's ear canal.

Preferably, the probe cover is adapted to be fixed to at least one section of either the head portion and/or the handle portion in such a way that the probe cover does not move relative to the handle portion during displacement of the electronic imaging unit and/or the infrared sensor unit by the motion mechanism. Otherwise, artifacts, such as earwax particles, adhering to the probe cover will obstruct a free view onto the eardrum, even if the electronic imaging unit and/or the infrared sensor unit is/are displaced by the motion mechanism.

The ear inspection device may further comprise a probe cover moving mechanism adapted to move at least a portion of the probe cover with respect to the electronic imaging unit and/or infrared sensor unit. Thus, artifacts, such as earwax particles, adhering to the probe cover and obstructing the view of the electronic imaging unit and/or infrared sensor unit onto the eardrum can be moved away from the electronic imaging unit and/or infrared sensor unit by the probe cover moving mechanism.

Preferably, the probe cover is designed in a way that allows unfolding or peeling off portions of the probe cover in order to move portions of the probe cover contaminated e.g. with earwax, away from the electronic imaging unit and/or infrared sensor unit. The otoscope preferably contains mechanical means to move the probe cover against the electronic imaging unit and/or infrared sensor unit or vice versa.

In order to illuminate the subject's ear canal and eardrum for taking images thereof, the ear inspection device may further comprise at least one light source also positioned at the distal end of the head portion, especially at the distal tip of the head portion, the otoscope preferably comprising a plurality of light sources at the distal end of the head portion, preferably with each of the light sources being separately controllable. The term "light source" is understood to apply to any source capable of emitting photons.

Since geometrical restrictions limit the space at the distal end of the head portion, the light source is preferably formed by the distal end of a light guide. For example, the light guide may exhibit a diameter of less than 1 mm, preferably of less than 0.5 mm, more preferably of about 0.2 mm. The light guide may be connected to an LED located remote from the distal end of the head portion. The light guide may be e.g. a nylon light guide, preferably having a diameter of only about 0.2 mm to 1 mm. Alternatively, a light source may be formed e.g. by a small light-emitting diode that is placed directly at the distal end of the head portion. However, attention should be paid that heat stemming from the light-emitting diode does not adversely affect the measurements of the infrared sensor unit. Therefore, it is preferred to locate the light-emitting diode remote from the infrared sensor element. For example, the infrared sensor unit may be located at the tip end of the head portion of the ear inspection device, whereas the light-emitting diode is located remote thereof having a light guide leading to the tip end of the head portion. Light guides usually filter out any infrared radiation, only emitting "cold" light.

It should be further mentioned that the infrared sensor unit may comprise some kind of heating and controlling mechanism so as to heat the infrared sensor unit to a predefined temperature before carrying out any measurements therewith. Thus, the accuracy of the measurement can be improved.

It is advantageous if the ear inspection device comprises a plurality of light sources at the distal end of the head portion, preferably with each light source being controllable separately. By illuminating objects in the subject's ear canal from different positions, e.g. by sequentially switching on and off the individual light sources, it is possible—as mentioned above—to distinguish different objects in the ear, without necessarily having to displace the electronic imaging unit by a motion mechanism within the ear canal.

Additionally or alternatively, the at least one light source may be controllable in view of the color, so that it is possible to change the color of the light emitted by the light source. For example, red color may be preferred to recognize an inflamed eardrum, wherein green color may be preferred to recognize earwax.

Like the electronic imaging unit and/or the infrared sensor unit, the at least one light source is preferably positioned radially offset from the longitudinal axis of the head portion. Such a configuration allows illumination of the eardrum without the need to introduce the light source as deeply into the ear canal as it would be necessary if the light source were placed centrally on the longitudinal axis of the head portion. The offset may be at least 1 mm, preferably at least 2 mm, more preferably at least 3 mm from the longitudinal axis.

According to one embodiment, the infrared sensor unit is arranged so as to maintain a predetermined distance with respect to the electronic imaging unit or at least one optical axis, even when the at least one optical axis is displaced by the motion mechanism. In case the infrared sensor unit is moved in conjunction with the at least one axis, a predefined spatial relationship allows for positioning the visual axis of the infrared sensor unit in a favorable eccentric position.

Preferably, the at least one light source is arranged so as to maintain a predetermined distance with respect to the electronic imaging unit, even when the electronic imaging unit is displaced by the motion mechanism. Such a configuration is advantageous because the predetermined distal relationship between the at least one light source and the electronic imaging unit allows for improved (automatic) image analysis. If a motion mechanism is provided, the motion mechanism preferably also displaces the at least one light source. If the light source is provided in the form of a light guide, the light guide should be sufficiently flexible to allow for such a displacement of the at least one light source.

According to another aspect, the present invention also refers to a corresponding method of determining a condition of a subject's ear, such as temperature, in particular at the subject's eardrum, wherein the method comprises the following steps:

introducing an ear inspection device, preferably the ear inspection device as described above, at least partially into the subject's external ear canal, the ear inspection device comprising an infrared sensor unit and an electronic imaging unit, wherein the electronic imaging unit exhibits at least one optical axis;

detecting infrared radiation from the subject's ear using the infrared sensor unit, wherein the infrared sensor unit exhibits a visual axis; and capturing at least one image based on radiation in the visible range, visible light, from the subject's ear using the electronic imaging unit, wherein capturing at least one image is carried out from at least one eccentric observation point positioned on the at least one optical axis eccentrically within the ear canal, and wherein detecting infrared radiation is carried out from a temperature detection point positioned on the visual axis and positioned centrically within the ear canal or positioned eccentrically within the ear canal within the same semicircle, especially the same quadrant of the cross section of the ear canal. Such a method or arrangement can ensure that both the infrared sensor unit and the optical axis are favorably arranged within the ear canal.

As described above, there exists a strong synergetic effect of detecting infrared radiation from the subject's ear combined with capturing at least one image based on radiation in the visible range from the subject's ear. That is, reliability and accuracy of the data acquired by the infrared sensor unit or the electronic imaging unit can be significantly improved by the data acquired by the respective unit.

The method according to the present invention may further comprise at least one of the following steps:
- verifying appropriate positioning of the ear inspection device with respect to the subject's ear based on the detected infrared radiation and/or the at least one captured image;
- determining whether the ear inspection device is positioned within the left or the right ear of the subject based on the at least one captured image; and
- discriminating different objects in the subject's ear, such as earwax, hair and the eardrum, by comparing their appearance in at least two images captured by the electronic imaging unit from different eccentric positions within the ear canal and/or with illumination from different positions, especially different eccentric positions, within the ear canal.

The method according to the present invention may further comprise applying a varying pressure within the ear canal during capture of at least two images. The otoscope may comprise pressurization means configured for applying the varying pressure within the ear canal, or the otoscope may be configured for being coupled with pressurization means and exhibits at least one gas conduit. The pressure is preferably applied by (compressed or evacuated) air, wherein a gas-tight chamber is formed by the subject's external ear canal and the corresponding device. A varying pressure allows fore identifying the eardrum more reliably. Preferably, gas is passed between the head portion and a probe cover put over the head portion. In particular, gas is passed between two shells of a double-ply probe cover. A double-ply probe cover provides high structural stability, even if the probe cover is made by deep-drawing. Preferably, the distal foil portion covering the camera is very thin and transparent, exhibiting a wall thickness of e.g. 30 micrometer (μm) to 50 micrometer, especially 20 micrometer. A double-ply probe cover facilitates pressurizing the ear canal at minimum risk of contamination or infection. At least one shell of the probe cover can be provided as a gas-tight shell. There is no need for the shell being gas-permeable. A gas-tight shell effectively insolates the ear canal from the head portion.

The method according to the present invention may further comprise detecting a fluid in the subject's ear using a fluid sensor unit, especially based on acoustic reflectance, tympanometry and/or otoacoustic emissions. The detection of fluid in the ear and/or abnormal low mobility represents another factor in the diagnosis of acute otitis media (OM), especially otitis media with effusion (OME), or severe ear infection. OME is defined by the presence of middle ear effusion, i.e. a liquid behind an intact tympanic membrane without signs or symptoms of acute infection. OME is one of the most frequent pediatric diagnoses. If fluid is accumulated behind the eardrum, or if the eardrum is bulged or retracted due to an abnormal air pressure in the middle ear, the latter cannot vibrate as freely as normally when subjected to pressure or acoustic waves. Therefore, the waves reflected from the eardrum will hardly be absorbed and/or attenuated by the eardrum. This can be determined e.g. by using an acoustic transducer and a microphone according to a technique known as "acoustic reflectance". This technique is described in detail in US patent document U.S. Pat. No. 5,868,682 B1, the content of which is also incorporated by reference herein. However, the technique of the fluid sensor unit may be based on any known technique, such as—but not limited to—acoustic reflectance, tympanometry and otoacoustic emissions.

For example, the fluid sensor unit may comprise pressurization means configured for applying a varying pressure within the subject's external ear canal. The fluid sensor unit can be coupled with the electronic imaging unit or can be provided as a component of the electronic imaging unit. Alternatively, according to one specific embodiment, the fluid sensor can be coupled with or can comprise optical means configured for detecting any fluid. According to one embodiment, the fluid sensor is provided separate from the electronic imaging unit. According to one specific embodiment, the fluid sensor as well as the optical means are provided separate from the electronic imaging unit. Using the fluid sensor unit in conjunction with the electronic imaging unit for determining the mobility of the eardrum allows for omitting the usually applied optical means for visual inspection (such as multiple lenses), thereby achieving another synergetic effect.

For hygienic reasons, the otoscope adapted for carrying out a method according to the present invention preferably further comprises an at least partially transparent probe cover configured to be put over the head portion. The probe cover may be made from a plastic material, preferably from a transparent plastic material. Such a probe cover may be designed as a single-use product that can be produced in larger numbers with low costs. The probe cover shall be transparent, at least at the locations where it covers the electronic imaging unit, so as to allow the electronic imaging unit to have a clear view onto the eardrum. The probe cover also inhibits contamination of the head portion of the otoscope comprising the electronic imaging unit, in particular when introducing the head portion into the subject's ear canal. Determining a condition of a subject's ear comprises identifying the eardrum based on the detected infrared radiation and on the at least one captured image may comprising the step of medically characterizing the eardrum based on the detected infrared radiation and on at least one captured image, in order to provide medical evidence of the eardrum, wherein medically characterizing the eardrum includes determining the degree of reddishness of the eardrum and/or indentifying objects within the tympanic cavity of the subject and/or determining a curvature, especially a convexity, of the eardrum and/or detecting the mobility of the eardrum during pressurizing the eardrum.

Medically characterizing the eardrum preferably is carried out automatically by the device, especially based on predefined ranges, e.g. with respect to temperature or a specific degree of reddishness. In other words: Medically characterizing the eardrum comprises at least one step of automatically evaluating the imaged captured by the electronic imaging unit, especially by means of a logic unit, e.g. based on one of the characteristics of the eardrum described above. Thereby, pre-diagnosis may be facilitated. Any more advanced or final disease diagnosis has to be carried out by the physician on the basis of other symptoms exhibited by the subject, which are observed by the physician, or by the physician's further examination.

In a method according to the present invention, preferably, medically characterizing the eardrum includes determining the degree of reddishness of the eardrum. Determining the eardrum's degree of reddishness can provide an index for assessing the likelihood of inflammation of the eardrum. Inflammation of the eardrum may suggest e.g. a (bacterial/viral) infection.

In a method according to the present invention, preferably, medically characterizing the eardrum includes indentifying objects within the tympanic cavity of the subject. In particular, any opaque body fluid, especially yellow body fluid, within the tympanic cavity can be evaluated as an indicator of a disease. It has been found that a relatively high intensity of illumination (transilluminating the eardrum) allows for (more reliable) acquisition of information relating to the medical condition of the patient. It has been found that any body fluid within the tympanic cavity evokes a higher degree of reflection. The fluid increases reflectance. In contrast, in case the tympanic cavity is empty, any light transilluminating the eardrum is only reflected with inferior intensity, as most of the light is absorbed within the tympanic cavity. Body fluid behind the eardrum, in particular yellow body fluid, can be evaluated as an indicator for otitis media with effusion (OME), i.e. the presence of middle ear effusion, i.e. a liquid behind the eardrum without signs or symptoms of acute infection. In particular, such body fluid can be evaluated as a precursor of an inflammation. Such body fluid may contain serous and/or mucous fluid containing white blood cells due to immune response to infection. In other words: transilluminating the eardrum and evaluating reflected light, especially in dependence on the intensity of illumination, can facilitate determining specific characteristics of the eardrum, e.g. an absolute degree of reddishness, such that the specific characteristics provide more information or more certain information with respect to the probability of any medical condition, e.g. an inflammation. This may help the layperson to decide as to whether a physician should be visited or not. Any more advanced or final disease diagnosis has to be carried out by the physician on the basis of other symptoms exhibited by the subject, which are observed by the physician, or by the physician's further examination.

In particular, the present invention is also based on the finding that the spectral composition of reflections of the eardrum can depend on the illumination level, i.e. the intensity of illumination. In particular, the degree of reddishness can increase with increasing intensity of illumination. The higher the intensity of illumination, the higher the degree of reddishness. Also, it has been found that at relatively high intensities of illumination, not only the eardrum, but also any other tissue can exhibit a high degree of reddishness. Therefore, observing the tympanic cavity can facilitate determining specific characteristics of the eardrum, e.g. an absolute degree of reddishness, such that the degree of reddishness provides more information or more certain information with respect to the probability of any inflammation, i.e. an inflammation index.

In a method according to the present invention, preferably, medically characterizing the eardrum includes determining a curvature, especially a convexity, of the eardrum. This allows for detecting bulging or retraction of the eardrum. This may facilitate identification of the eardrum. This may also facilitate diagnosis, as in case of body fluid within the tympanic cavity (which is an indicator for specific medical conditions), the curvature of eardrum is convex, indicating an increased pressure within the middle ear. A high amount of body fluid evokes a convex curvature, i.e. towards the otoscope. Bulging or retraction may be an indicator for a specific medical condition or disease, e.g. for OME.

In a method according to the present invention, preferably, medically characterizing the eardrum includes pressurizing the eardrum. For example, an otoscope for carrying out the method may comprise pressurization means, e.g. a pressure transducer or a pump, configured for applying a varying pressure within the subject's external ear canal. This technique is also known as "pneumatic otoscopy". Preferably, the electronic imaging unit itself is configured for inspecting the mobility of the subject's eardrum when exposed to the varying pressure. The pressure is preferably applied by (compressed) air, wherein an air-tight chamber is formed by the subject's external ear canal and the corresponding device, i.e. the head portion or a probe cover put over the head portion.

In a method according to the present invention, preferably, medically characterizing the eardrum includes detecting the mobility of the eardrum. An otoscope for carrying out a method according to the present invention may comprise a fluid sensor unit adapted to detect fluid in the subject's ear, especially a fluid sensor unit configured for detection based on acoustic reflectance, tympanometry and/or otoacoustic emissions. The detection of fluid in the ear and/or abnormal low mobility represents another factor in the diagnosis of acute otitis media (OM), especially otitis media with effusion (OME), or severe ear infection. OME is defined by the presence of middle ear effusion, i.e. a liquid behind an intact tympanic membrane without signs or symptoms of acute infection. OME is one of the most frequent pediatric diagnoses. If fluid is accumulated behind the eardrum, or if the eardrum is bulged or retracted due to an abnormal air pressure in the middle ear, the latter cannot vibrate as freely as normally when subjected to pressure or acoustic waves. Therefore, the waves reflected from the eardrum will hardly be absorbed and/or attenuated by the eardrum. This can be determined e.g. by using an acoustic transducer and a microphone according to a technique known as "acoustic reflectance". This technique is described in detail in US patent document U.S. Pat. No. 5,868,682 B1, the content of which is also incorporated by reference herein. However, the technique of the fluid sensor unit may be based on any known technique, such as—but not limited to—acoustic reflectance, tympanometry and otoacoustic emissions.

For example, the fluid sensor unit may comprise pressurization means configured for applying a varying pressure within the subject's external ear canal. The fluid sensor unit can be coupled with the electronic imaging unit or can be provided as a component of the electronic imaging unit. Alternatively, according to one specific embodiment, the fluid sensor can be coupled with or can comprise optical means configured for detecting any fluid. According to one embodiment, the fluid sensor is provided separate from the electronic imaging unit. According to one specific embodiment, the fluid sensor as well as the optical means are provided separate from the electronic imaging unit. Using the fluid sensor unit in conjunction with the electronic imaging unit for determining the mobility of the eardrum allows for omitting the usually applied optical means for visual inspection (such as multiple lenses), thereby achieving another synergetic effect.

In a method according to the present invention, preferably, identifying objects comprises identifying the eardrum, the method further comprising the step of medically characterizing the eardrum based on at least one image captured of the eardrum, in order to provide medical evidence of the eardrum. This may help the layperson to decide as to whether a physician should be visited or not. The method according to the present invention may provide the user with a calculated "risk index" for middle ear disease, calculated by a logic unit from image information.

In a method according to the present invention, preferably, medically characterizing the eardrum includes determining the degree of reddishness of the eardrum. Determining the eardrum's degree of reddishness can provide an index for assessing the likelihood of inflammation of the eardrum. Inflammation of the eardrum may suggest e.g. a (bacterial/viral) infection.

According to a further aspect, the present invention also refers to a method of determining the temperature of a subject's eardrum and medically characterizing the eardrum, wherein the method comprises the following steps:

- introducing an ear inspection device, preferably the ear inspection according to one of the embodiments of the present invention, at least partially into the subject's external ear canal, the ear inspection device comprising an infrared sensor unit and an electronic imaging unit, wherein the electronic imaging unit exhibits at least one optical axis;
- detecting infrared radiation from the eardrum using the infrared sensor unit, wherein the infrared sensor unit exhibits a visual axis; and
- capturing at least one image based on radiation in the visible range from the eardrum using the electronic imaging unit, wherein capturing at least one image is carried out from at least one eccentric observation point positioned on the at least one optical axis eccentrically within the ear canal, and wherein detecting infrared radiation is carried out from a temperature detection point positioned on the visual axis and positioned centrically within the ear canal or positioned eccentrically within the ear canal within the same semicircle, especially the same quadrant of the cross section of the ear canal, wherein the method further comprises the following step:
- determining color information or brightness and color information in the at least one image of the eardrum by a logic unit, in order to automatically medically characterizing the eardrum, wherein medically characterizing the eardrum includes determining the spectral composition of reflections of the eardrum. Such a method allows for correlation medical information acquired (automatically) by the electronic imaging unit with medical information acquired (automatically) by the infrared sensor unit, especially in order to provide more reliable medical information to a user, in particular a layperson.

Medically characterizing the eardrum may comprise diagnosing an ear disease. Such a diagnostic method may comprises all steps of the previously described inventive method of determining a condition of a subject's ear. The inventive method may form part of the inventive diagnostic method. Firstly, objects shown in the at least on captured image may be identified (and distinguished from other objects in the subject's ear), and then the status (especially the temperature) of at least one of the identified objects is determined. Such a diagnostic method may even allow for reliably diagnosing e.g. an inflammation of the eardrum without the need of assistance of a skilled physician. An otoscope adapted for carrying out the diagnostic method according to the present invention may automatically detect and identify the eardrum, medically characterize the detected eardrum, and inform the user (who may be a layperson) about a medical condition of the eardrum, e.g. whether the eardrum is inflamed or not. Such a diagnostic method may further also comprise at least some of the preferred features of the method of identifying objects in a subject's ear, as described in detail above.

DESCRIPTION OF THE FIGURES

Exemplary embodiments of an ear inspection device according to the present invention will be described in more detail in the following with respect to the drawings, wherein:

FIG. 1 schematically shows a cross-sectional view of a head portion and of a part of a handle portion of a first embodiment of an ear inspection device according to the present invention;

FIG. 2 shows an enlarged view of a plate covering a bore provided in the head portion illustrated in FIG. 1;

In case any reference sign is not explicitly described in a respective figure, it is referred to the other figures. In other words: like reference characters refer to the same parts or the same type or group of device throughout the different views.

DESCRIPTION OF PREFERRED EMBODIMENTS

Figure 3:
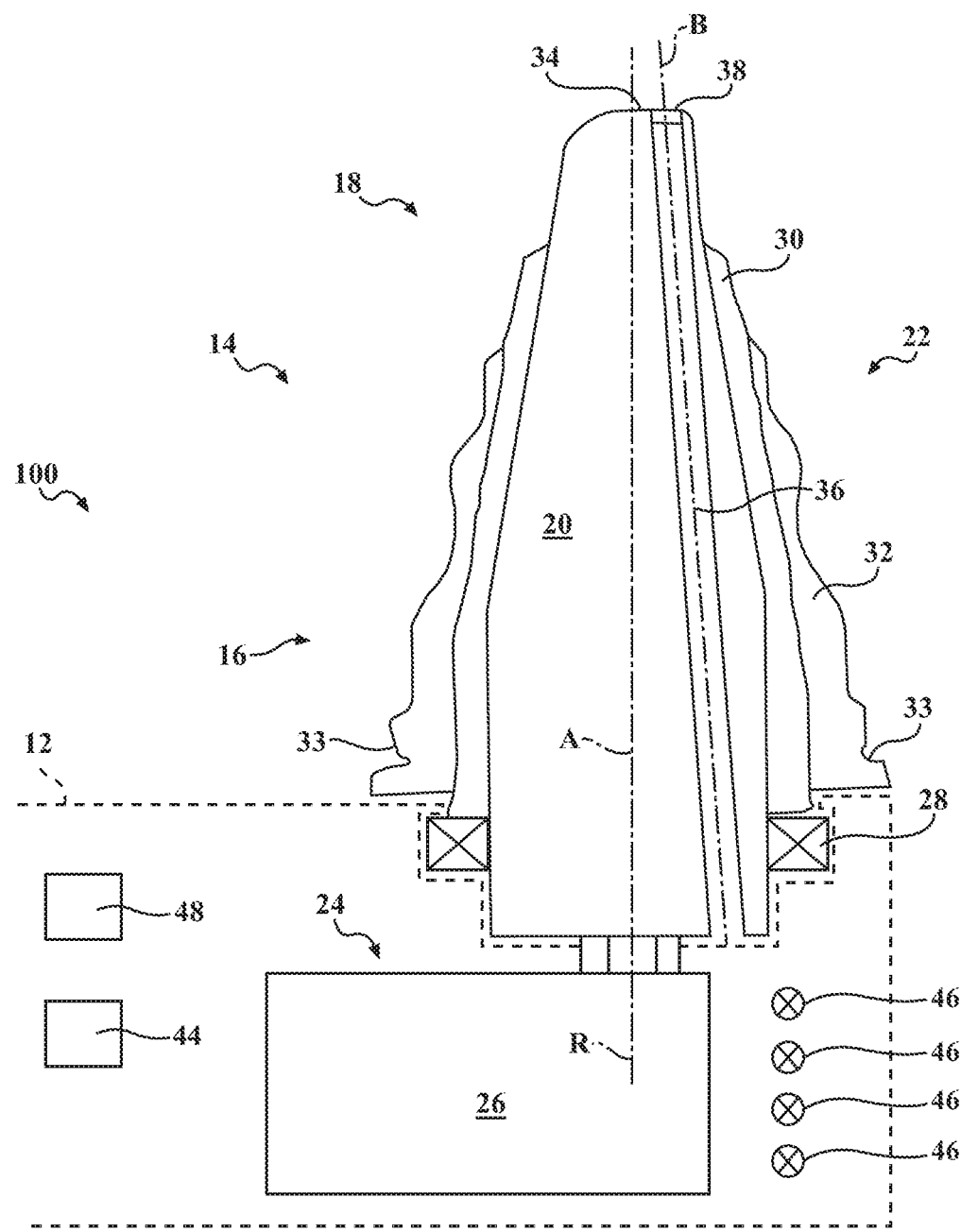
FIG. 3 schematically shows a cross-sectional view of a head portion and of a part of a handle portion of a second embodiment of an ear inspection device according to the present invention.

FIG. 1 schematically shows a cross-sectional view of a head portion 14 and a part of a handle portion 12 (only shown in phantom lines) of a first embodiment of an ear inspection device 10 according to the present invention. As can be seen from FIG. 1, the head portion 14 has a substantially tapering form extending along a longitudinal axis A of the head portion 14. The head portion 14 comprises a relatively large proximal end 16 adjacent to the handle portion 12 and a smaller distal end 18. The distal end 18 of the head portion 14 is adapted to be introduced into a subject's ear canal.

Furthermore, the head portion 14 comprises a rotatable, radial inner portion 20 and a fixed, radial exterior portion 22. The rotatable portion 20 is rotatable about an axis of rotation R which—in the shown exemplary embodiment—corresponds to the longitudinal axis A of the head portion 14. A motion mechanism 24 comprising a servo motor 26 is positioned within the handle portion 12 and is coupled to the rotatable portion 20 of the head portion 14, so as to rotate the rotatable portion 20 about its axis of rotation R relative to the fixed portion 22 of the head portion and relative to the handle portion 12 of the ear inspection device 10. The rotatable portion 20 is supported by a radial bearing 28 (also only schematically shown).

In the shown exemplary embodiment, the exterior portion 22 of the head portion 14 comprises a support structure 30 providing the required stability of the head portion 14. The support structure is at least partially covered by an outer cladding 32 formed from a relatively soft material, such as silicone. The cladding 32 makes the introduction of the distal end 18 of the head portion 14 into his ear canal more comfortable for the subject. The cladding may comprise a circular slot-like recess 33 adapted to engage with a complementarily formed circular tongue of a (not shown) probe cover. The probe cover may be formed from a plastic material and may be adapted to be put over the head portion 14. Preferably, the probe cover is formed from a transparent material, preferably transparent to both, visible and infrared light. Its wall may be relatively thin, thereby making the probe cover relatively flexible. At least a portion of the probe cover covering the distal end 18 of the head portion 14 should be transparent, so as to allow an electronic imaging unit and an infrared sensor unit (described in the following) which are located at the distal end 18 of the head portion 14 to have a free view through the probe cover. For hygienic reasons, the probe cover is preferably designed as a single-use product. The probe cover also reliably inhibits contamination of the distal end 18 comprising the electronic imaging unit and the infrared sensor unit. Without such a probe cover there is a high risk that e.g. earwax particles may adhere to the electronic imaging unit and/or the infrared sensor unit (thereby deteriorating the detection quality thereof) when introducing the distal end 18 into the outer part of the subject's exterior ear canal.

The head portion 14 comprises a distal end point 34 which, in the shown exemplary embodiment, is located substantially on the longitudinal axis A of the head portion 14. However, the head portion 14 may alternatively have a tapering shape that is not substantially symmetrical to its longitudinal axis A (as shown in FIG. 1) but is more adapted to the anatomy of the human ear canal.

Irrespective of the precise shape of the head portion 14, the head portion 14 is preferably dimensioned in such a way that it cannot be introduced into the inner part of the outer ear canal of the subject's outer ear. In the shown exemplary embodiment, the distal end 18 of the head portion 14 has a substantially round shape. Only a few millimeters (less than 4 mm) away from the distal end point 34 in the direction of the longitudinal axis A, the head portion 14 exhibits a diameter of more than 5 mm. Since the inner part of the outer ear canal of an adult usually exhibits a diameter of 4 mm, there is no risk that the distal end 18 of the head portion 14 is inadvertently introduced too deeply into the subject's ear canal. Therefore, injuries to the sensitive skin of the inner part of the outer ear canal and/or to the eardrum can be reliably avoided.

The movable portion 20 comprises a first bore 36 extending substantially along the axial direction A of the head portion 14, but not exactly parallel thereto. The distal end of the first bore 36 is located in proximity to the distal end point 34, but is offset with its bore axis B by at least 2 mm from the longitudinal axis A. Furthermore, the distal end of the first bore 36 is closed by a plate 38. An enlarged top view of the plate 38 is shown in FIG. 2. Since the bore 36 is cylindrical in shape, in FIG. 2 the plate 38 has a generally circular appearance with the bore axis B forming the center thereof. However, the bore 30 and/or the plate 38 may equally exhibit other shapes.

The plate 38 supports an electronic imaging unit 40 comprising a wide-angle color video camera 40.1 and distal ends of four light guides 42. In the exemplary embodiment, the light guides 42 are located around the video camera 40.1, such that one light guide 42 is associated to each of the four lateral sides of the substantially rectangular video camera 40.1. However, this is not a prerequisite for the present device. Instead of four light guides 42, for example, only two light guides 42 may be provided in the ear inspection device 10. The video camera 40.1 is advantageously a wafer-level camera of dimensions in the 1 to 2 mm range having a substantially flat configuration. The wafer-level camera advantageously exhibits dimensions of only about 1 mm×1 mm providing a resolution of about 250 pixels×250 pixels. The plate 38 has a diameter between 1.5 mm and 2.0 mm and the light guides 42 have a diameter of only about 0.2 mm.

The video camera 40.1 is connected to a distal end of a cable (not shown). The cable, e.g. a ribbon cable, extends through the bore 36 and into the handle portion 12 of the ear inspection device 10. A distal end of the cable is connected to a logic unit 44, such as a microprocessor, which is schematically illustrated in FIG. 1. Similarly, the light guides 42 (not shown in FIG. 1) extend through the bore 36 and into the handle portion 12 of the ear inspection device 10. Proximal ends of the light guides 42 are connected to four LEDs 46, respectively. The LEDs 46 are positioned—like the logic unit 44—within the handle portion 12 of the ear inspection device 10. The LEDs 46 can be individually switched on and off. Furthermore, the handle portion 12 preferably comprises a memory 48 for storing images captured by the video camera 40.1. The memory may be formed e.g. by a storage card slot and a corresponding storage card inserted in the slot. The handle portion 12 may further comprise a display (not shown) for displaying to the user the images taken by the camera 40.1. Additionally or alternatively, the handle portion 12 may comprise a cable connection port, such as an USB-port, and/or a wireless connection, such as Bluetooth®, WIFI® and/or an energy supply, such as a (rechargeable) battery. These additional (optional) components of the handle portion 12 are known e.g. from modern digital cameras or mobile phones.

The first embodiment of the inventive ear inspection device 10 further comprises a second bore 50 extending along the longitudinal axis A, i.e. the axis of the second bore substantially coincides with the longitudinal axis A. Consequently, in this embodiment, the distal end of the second bore 50 substantially coincides with the distal end point 34 of the head portion 14. The distal end of the second bore 50 is closed by a plate comprising an infrared sensor unit 52 (only schematically shown herein) configured for detecting infrared radiation from the subject's ear. The infrared sensor unit 52 is connected to a distal end of a cable (not shown). The cable, e.g. a ribbon cable, extends through the second bore 50 and into the handle portion 12 of the ear inspection device 10. A distal end of the cable is also connected to the logic unit 44.

The main viewing direction X5 of the infrared sensor unit 52 (i.e., an visual axis X5 of infrared sensor unit) substantially corresponds to the longitudinal axis A and, thus, is angled to the main viewing direction of the electronic imaging unit 40, substantially corresponding to the bore axis B of the first bore 36. The two main viewing directions A and B preferably intersect at a point at which the subject's eardrum is supposed to be when the ear inspection device is properly introduced into the subject's exterior ear canal. In view of the typical length of the inner part of the subject's exterior ear canal, the distance may be between 3 mm and 20 mm.

The ear inspection device 10 shown in FIGS. 1 and 2 may be used e.g. to detect the subject's body core temperature (i.e. the temperature at the eardrum) and/or to visually inspect the condition of the eardrum by capturing images thereof, e.g. in order to determine the likelihood of an inflammation thereof. Preferably, data of the subject's ear is acquired (preferably simultaneously or in close temporal relationship) by both units, i.e. by the infrared sensor unit 52 and the electronic imaging unit 40, so that the data acquired by one unit can be used to verify the data acquired by the respective other unit. Performing such a plausibility check allows for avoiding misleading or wrong results. Thus, the reliability and accuracy of the corresponding measurement can be increased. In particular, it is possible to assure with high reliability that the ear inspection device 10 is correctly positioned or oriented with respect to the subject's ear so as to assure that the main viewing directions of the units 40, 52 are pointing onto the eardrum.

For acquiring data of a subject's inner part of the external ear canal, and in particular of a subject's eardrum, the distal end 18 of the head portion 14 has to be introduced into the subject's ear canal. Due to the shape of the head portion 14 there is no risk to insert the distal end 18 too deeply into the ear canal. That is, the shape and geometry of the distal end 18 do not allow too deeply introducing the distal end point 34 into the subject's inner part of the outer ear canal which is pain sensitive. Therefore, injuries to the skin of the inner part of the outer ear canal and/or the eardrum can be reliably avoided. The geometry and the technology of the inventive ear inspection device do not require deforming the subject's ear as with a classic ear inspection device, as described above. Consequently, the ear inspection device according to the present invention can also be securely applied by lay persons.

Even though the distal end 18 of the head portion 14 will not be inserted into the inner part of the outer ear canal, the ear inspection device according to the present invention, nevertheless, allows for capturing images from the inner part of the outer ear canal and the eardrum, due to the wide angle camera 40.1 being provided at the distal end 18 of the head portion 14. In order to improve the ability of the camera 40.1 to "see" the eardrum, the camera 40.1 is placed offset from the longitudinal axis A of the head portion 14. Furthermore, the main "viewing direction" of the camera 40.1, corresponding to the bore axis B, is angled with respect to the longitudinal axis A of the head portion 14. The bore axis B and the longitudinal axis A intersect at a point having a predetermined distance from the distal end point 34, wherein the predetermined distance corresponds to the typical length of a subject's inner part of the outer ear canal, so that the camera 40.1 is directed to the eardrum.

When the distal end 18 of the head portion is introduced into the subject's ear canal, it may happen that artifacts, such as earwax particles or hair, in front of the camera 40.1, e.g. adhering to the probe cover, partially or even fully obstruct the view onto the eardrum. Therefore, the motion mechanism 24 may turn the rotatable portion 20 of the head portion 14 about its axis of rotation R with respect to the remaining ear inspection device 10. For example, the motion mechanism 24 may rotate the rotatable portion 20 from an initial position by about 120° in clockwise direction, then from the initial position by about 120 in counter-clockwise direction, and finally return to the initial position. The camera 40.1 may capture one or more images from each of these equally spaced three positions. The logic unit 44 may identify different objects in the subject's ear by comparing the images received from the camera 40.1. In particular, the logic unit 44 may discriminate artifacts from the eardrum by determining their distance to the camera 40.1 according to the principle of stereoscopic viewing, as described in more detail above.

In order to further improve the identification process, more than one image may preferably be taken from each of the three positions of the camera 40.1, with different LEDs 46 switched on and off for each captured image. Illumination of the artifacts and the eardrum from different positions also assists to discriminate these objects, as described in more detail above.

Finally, a new image may be generated (preferably by the logic unit 44) in which the identified artifacts are eliminated, so as to clearly show the eardrum. The logic unit may discriminate image pixel areas that change their brightness values above a certain threshold when switching between LEDs 46 illuminating from different positions. Further, the logic unit may determine areas which depict objects close to (in the close proximity of) the distal tip by evaluating their reflection intensity. The logic unit may calculate a "mosaic" image, especially by using pixel information from different images taken at different illumination angles, in order to optimize exposure of areas of interest and/or in order to eliminate any obstructive object in the foreground, like e.g. hair and earwax particles. In order to create such "mosaic" or "stitched" or "composed" image, pixel information from separate images as well as from the same image may be averaged, subtracted, added, multiplied, and/or normalized. The spectral composition of the reflections of the eardrum, especially the degree of reddishness, can then be easily determined, especially based on any such image evaluation method as describes above. The user may be provided with corresponding information, such as to see the physician because of the risk of otitis media, or not. Also, if the ear inspection device failed to detect the eardrum because of massive earwax in the subject's ear canal, corresponding information may be provided to the user. The user may then decide to visit a physician for having his or her ear canal cleaned. Also the data acquired by the infrared sensor element 52 can be advantageously taken into account by the logic unit 44 in order to inform the operator of the ear inspection device 10 correspondingly.

As mentioned above, in the first embodiment of the inventive ear inspection device 10 shown in FIGS. 1 and 2, the main viewing direction of the infrared sensor unit 52 substantially coincides with the longitudinal axis A of the head portion 14. Therefore, the infrared sensor unit 52 is not able to "look around the corner" to the same extend as the electronic imaging unit 40.

Figure 4:
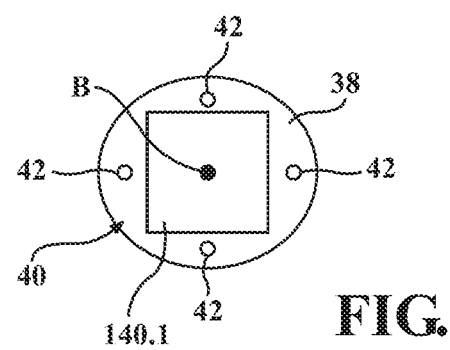
FIG. 4 shows an enlarged view of a plate covering a bore provided in the head portion illustrated in FIG. 3.
Figure 5:
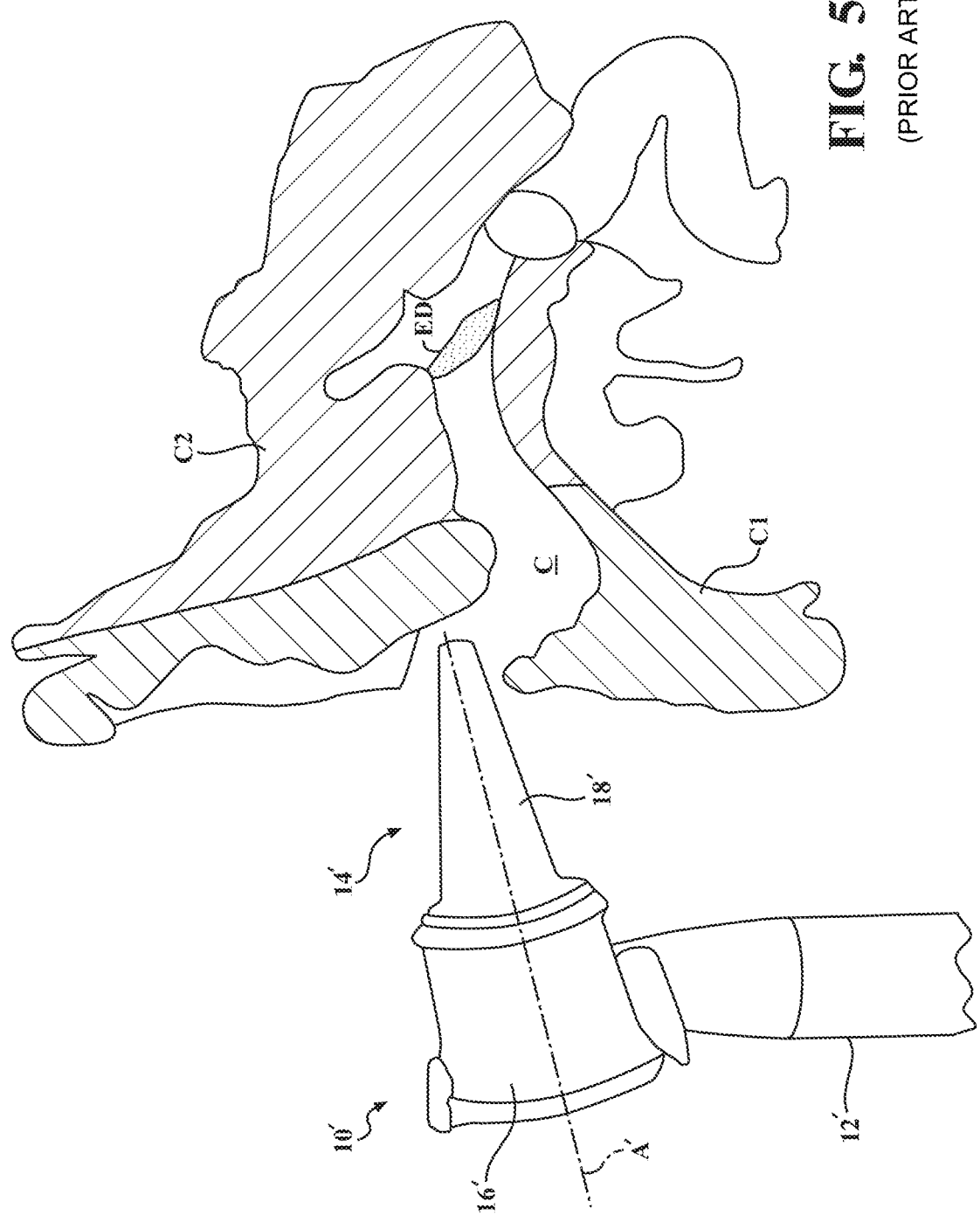
FIG. 5 shows an otoscope of the prior art, with its head portion partially introduced into the subject's ear canal.
Figure 6:
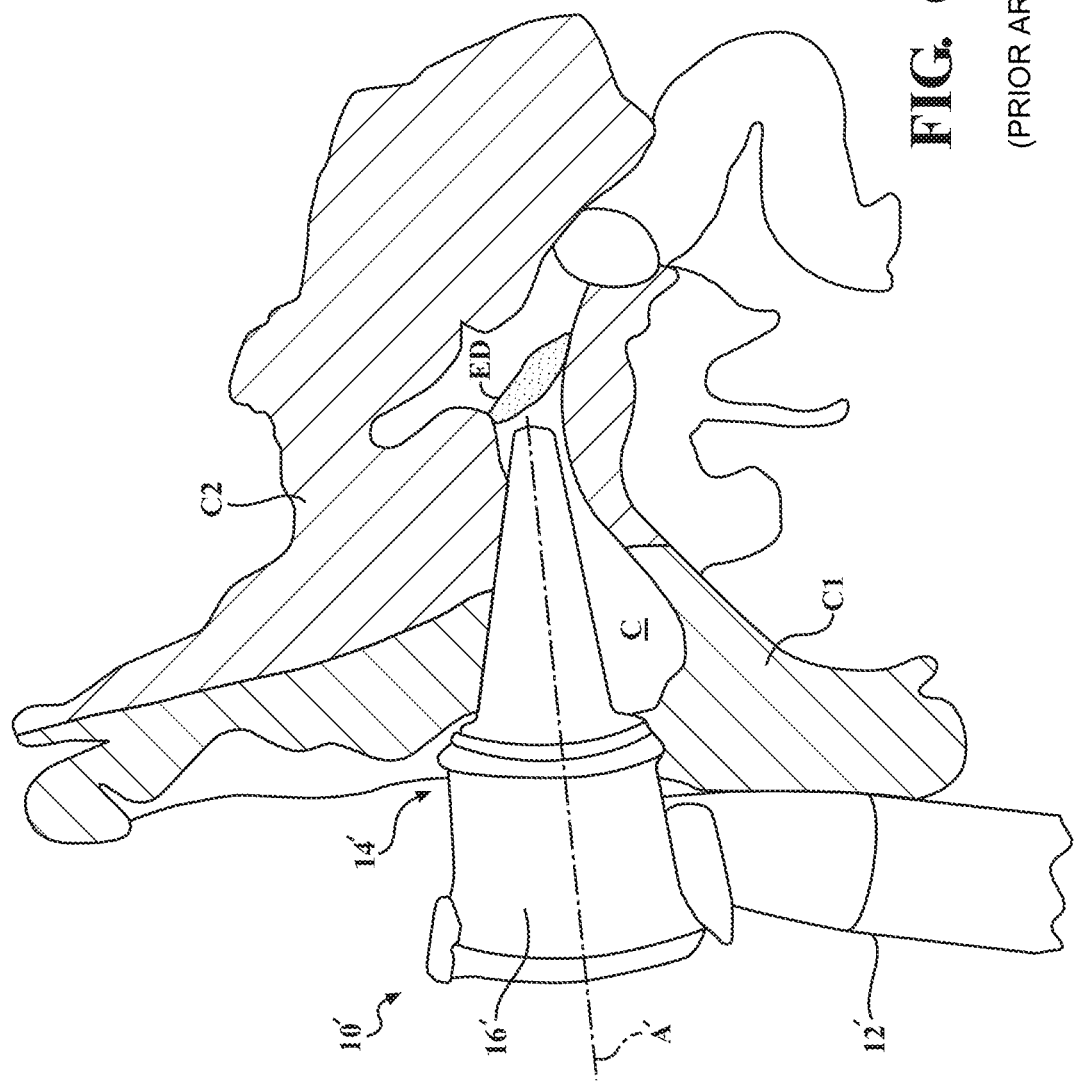
FIG. 6 shows the otoscope of FIG. 5 with its head portion fully introduced into the subject's ear canal.

A further improved second embodiment of an inventive ear inspection device 100 is shown in FIGS. 3 and 4. Like reference signs refer to the same parts as in the first embodiment. Therefore, a detailed description thereof is omitted here. The second embodiment differs from the first embodiment substantially only in that it does not comprise the second bore 50 with the cover plate having the infrared sensor unit 52. Instead, the infrared sensor unit 140 is formed integrally with the electronic imaging unit 140. That is, element 140 corresponds to or comprises a wafer-level camera capable of acquiring both, pictures of light in the visible range and pictures of light in the infrared range. Therefore, in this embodiment, both the electronic imaging unit and the infrared sensor unit are capable of "looking around the corner". Furthermore, the main viewing directions of both units coincide, as both units 140 are provided on the same chip.

Figure 7:
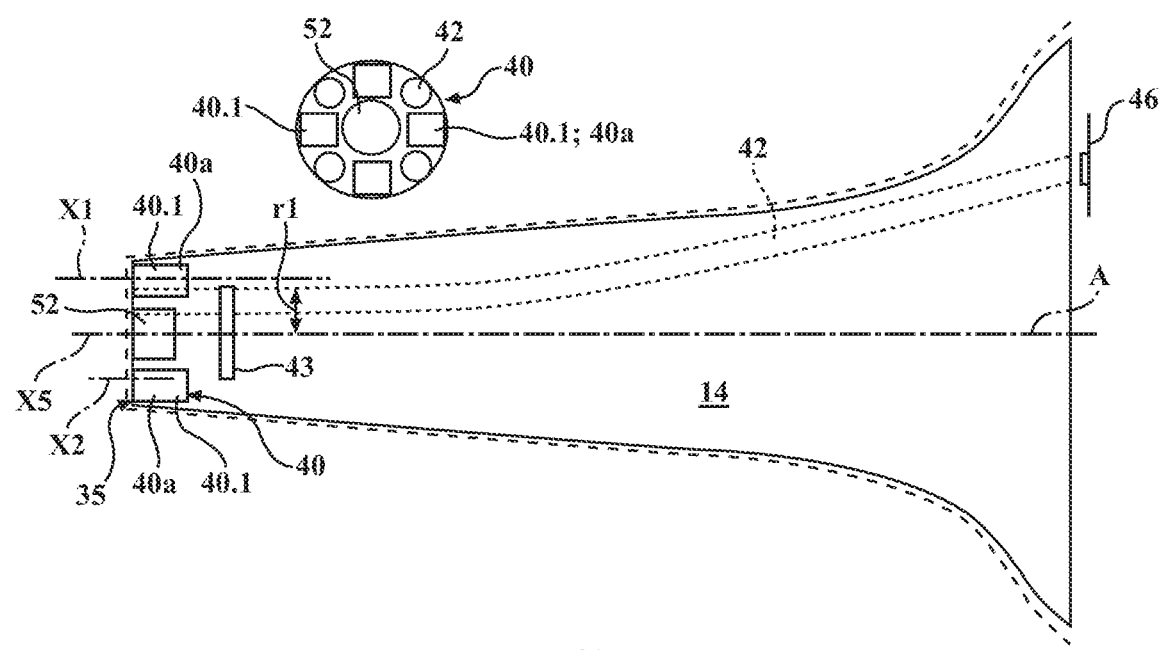
FIG. 7 schematically shows a cross-sectional side view of the head portion of an embodiment of an otoscope according to the present invention as well as a front view on the distal tip of the head portion.

FIG. 7 shows a head portion 14 including at least one light guide 42 or light source and an electronic imaging unit 40 comprising several eccentrically arranged, i.e. radially offset miniature cameras 40.1. Light is guided from one or more light sources 46 via the light guide 42 to a distal tip 35 of the head portion 14. The cameras 40.1 are arranged in a radial distance r1 between a longitudinal axis A of the head portion 14 and an optical axis X1, X2 of the respective camera 40.1. The (eccentric) distance r1, i.e. the radial offset is preferably in the range of 1 mm to 2.5 mm. At the distal tip 35, an infrared sensor unit 52 is arranged centrically. The infrared sensor unit 52 exhibits or defines a visual axis X5. In addition to the cameras 40.1 or in conjunction with the cameras 40.1, an image sensor 43 can be provided, especially in conjunction with beam splitter optics. As an alternative, optical components like lenses or mirrors of beam splitter optics can replace one or more of the cameras 40.1. Alternatively or in addition to the infrared sensor unit 52, a fluid sensor unit or mobility sensor 40a may be arranged at the distal end, as described in context with FIG. 8.

Figure 8:
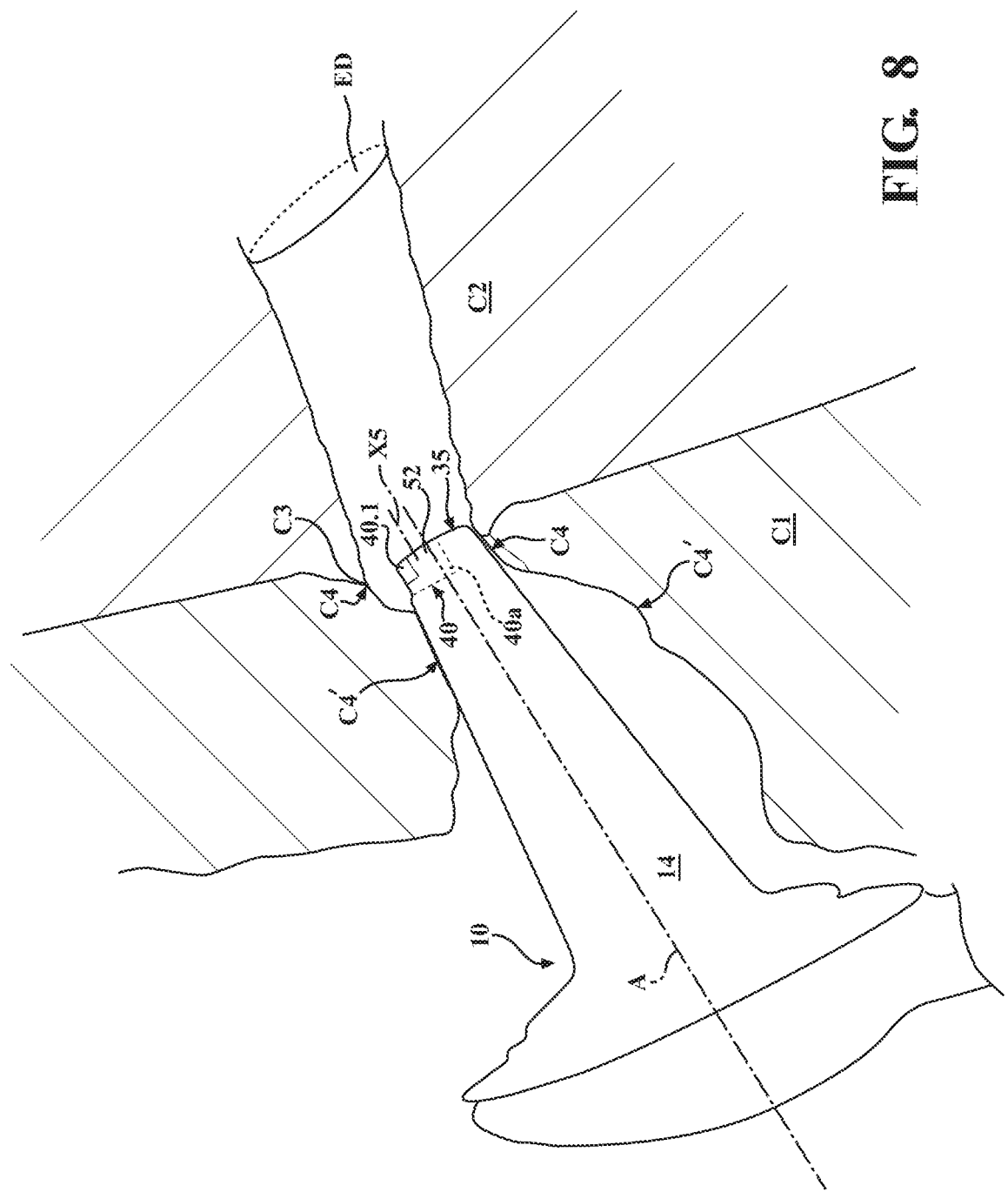
FIG. 8 schematically shows an otoscope according to the present invention with its head portion introduced into the patient's ear canal as far as to an end position from which the ear drum can be observed.

FIG. 8 shows an ear canal C which has an S-shaped (sigmoid) form with a first curvature C4' (which has been "straightened" to some extend) and a second curvature C4, the second curvature C4 being closer to the ear drum ED than the first curvature C4'. A head portion 14 of an otoscope 10 is introduced within the ear canal C. The otoscope 10 is introduced within the ear canal C as far as the second curvature C4, i.e. roughly as far as a transition area C3 between soft connective tissue C1 and hard bone C2. In the position shown in FIG. 8, the otoscope 10 is able to "look around the corner". The "corner" can be defined as the second curvature C4 of the ear canal C. At a distal tip 35 of the otoscope, both an infrared sensor unit 52 as well as a miniature camera 40.1, which is a component of an electronic imaging unit 40, are arranged radially offset with respect to a longitudinal axis of the head portion 14. Alternatively or in addition to the infrared sensor unit 52, a fluid sensor unit or mobility sensor 40a may be arranged at the distal end. The fluid sensor unit or mobility sensor 40a may be integrated in the electronic imaging unit 40, i.e., the fluid sensor unit or mobility sensor 40a may be provided as a component of the electronic imaging unit 40.

Figure 9:
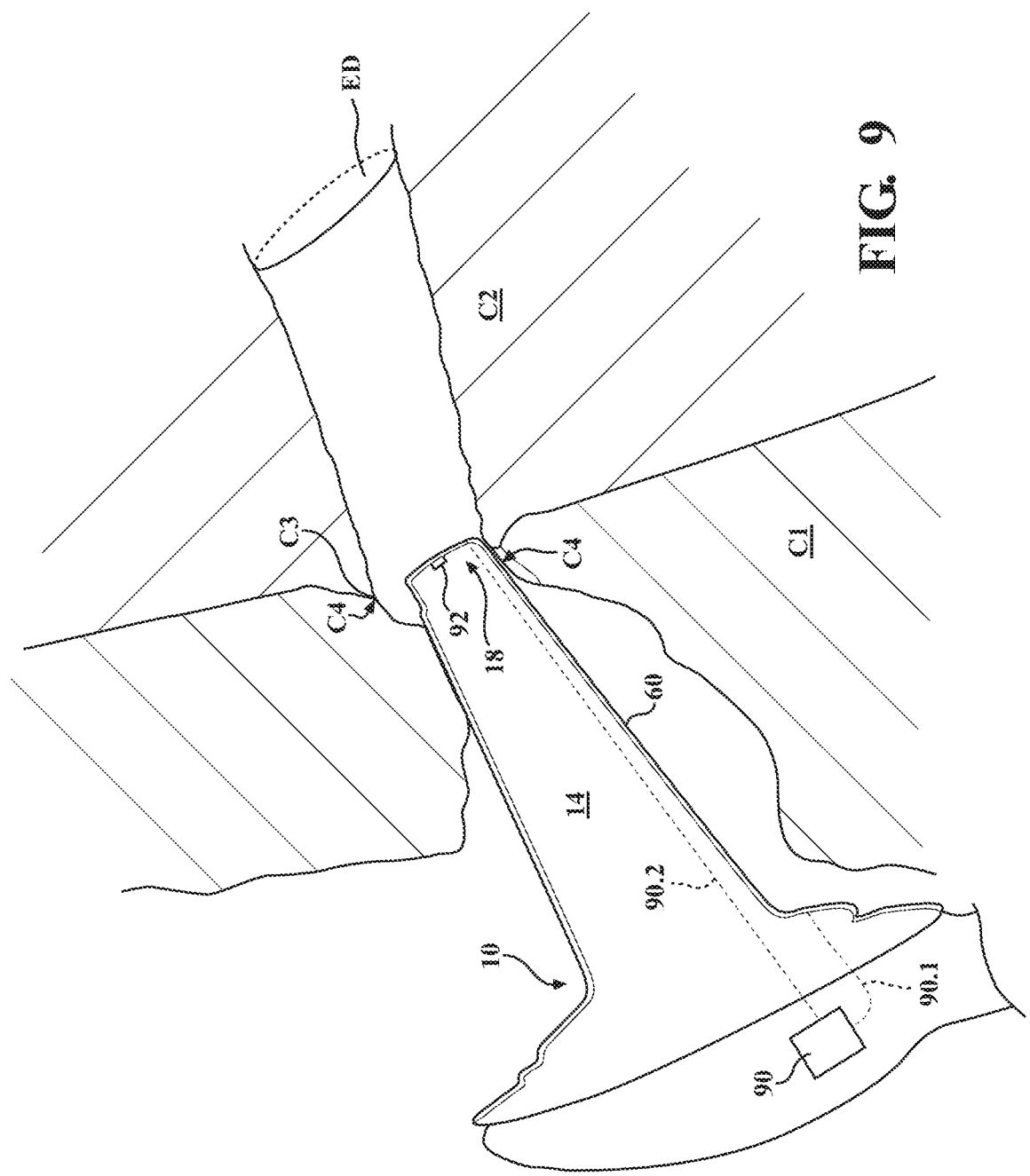
FIG. 9 schematically shows an otoscope according to the present invention, with its head portion introduced into the patient's ear canal as far as to an end position from which the ear drum can be observed.

FIG. 9 shows an ear canal C which has an S-shaped (sigmoid) form with a first curvature C4' (which has been "straightened" to some extend) and a second curvature C4, the second curvature C4 being closer to the ear drum ED than the first curvature C4'. A head portion 14 of an otoscope 10 is introduced within the ear canal C. The otoscope 10 is introduced within the ear canal C as far as the second curvature C4, i.e. roughly as far as a transition area C3 between soft connective tissue C1 and hard bone C2. In the position shown in FIG. 9, the otoscope 10 is able to "look around the corner". The "corner" can be defined as the second curvature C4 of the ear canal C. The otoscope 10 exhibits pressurizing means 90 comprising at least one first pressure line 90.1 coupling the pressurizing means 90 with an outer lateral surface of the head portion 14 as well as at least one second pressure line 90.2 coupling the pressurizing means 90 with a front side, i.e. a distal tip arranged at a distal end 18 of the head portion 14. At the distal tip, a pressure sensor 92 is arranged which allows for detecting a pressure within the ear canal between the head portion 14 and the eardrum ED. The position of the pressure sensor 92 may be different from the position shown in FIG. 9. A single-ply or double-ply probe cover 60 covers the head portion 14. The pressurizing means 90 allow for passing gas through the probe cover 60, be it through cavities between an inner and an outer shell of the probe cover 60, be it through at least one porous section of a single shell or through one of an inner and an outer shell of a double-ply probe cover, especially in order to exert a pressure on the eardrum ED.

Figure 10:
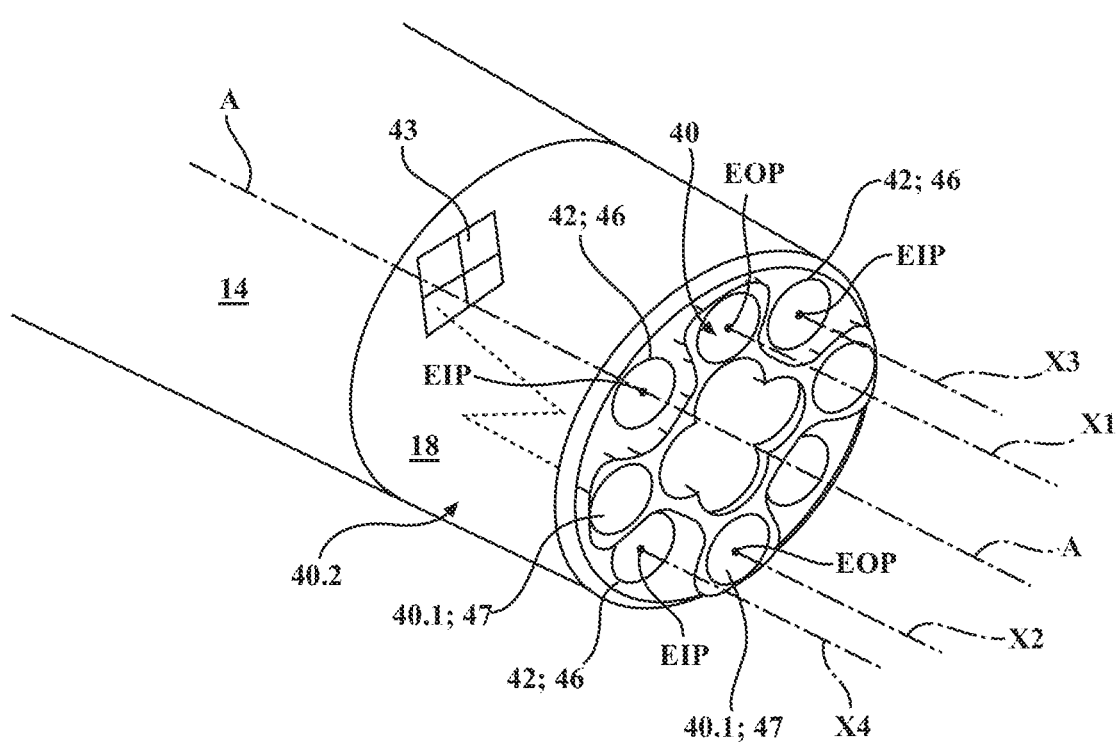
FIG. 10 schematically shows a perspective side view of a head portion of an ear inspection device which can be used in context with embodiments according to the present invention.

FIG. 10 shows a head portion 14 of an otoscope, wherein at a distal end 18, an electronic imaging unit 40 is arranged. The electronic imaging unit 40 exhibits a plurality of optical axes X1, X2 as well as a, plurality of illumination axes X3, X4, each axis X1, X2, X3, X4 being arranged radially offset with respect to a longitudinal axis A of the head portion 14. The plurality of optical axis X1, X2 may be provided by beam splitter optics 40.2 of the electronic imaging unit 40, at least partially. The radial position of the illumination axes X3, X4 can be defined by an eccentric illumination point HP, respectively. The radial position of the optical axes X1, X2 can be defined by an eccentric observation point EOP, respectively. The beam splitter optics 40.2 may comprise a plurality of lenses 47 and/or mirrors which are configured for providing radially offset (eccentric) observation points EOP (as schematically illustrated by the dashed line). The beam splitter optics 40.2 optically couple the lenses 47 with an image sensor 43. The respective eccentric illumination point EIP is centrically arranged at a front surface of a light guide 42 or light source or LED 46. The respective eccentric observation point EOP is centrically arranged at a front surface of a camera 40.1 or any other optical component or lens 47 of the electronic imaging unit 40. The optical components 47 can be in optical communication with the single image sensor 43 of the electronic imaging unit 40, which is preferably centrically arranged, as schematically illustrated in FIG. 10. The image sensor 43 may be provided with different sections or segements, e.g. four segments (as schematically illustrated), in order to provide one section for one optical axis, respectively.

Figure 11:
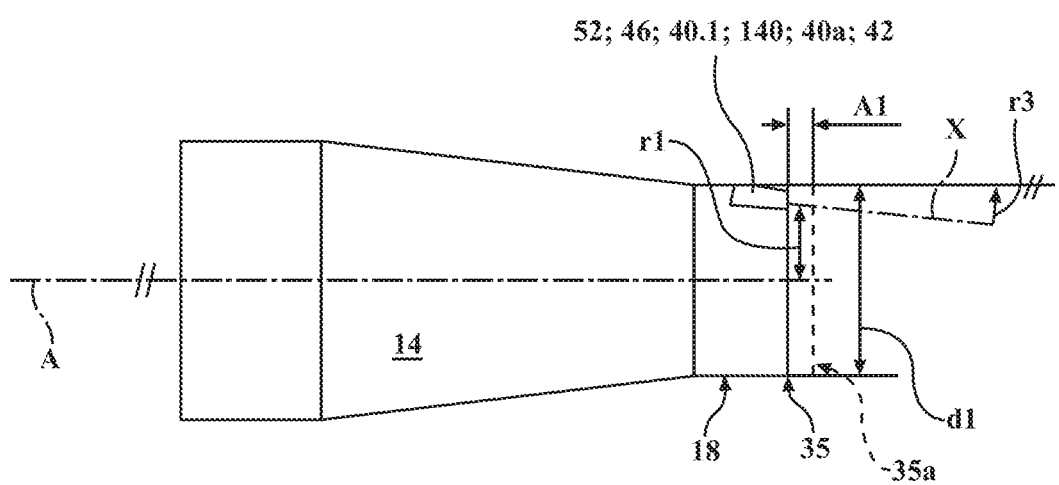
FIG. 11 schematically shows a head portion of an ear inspection device according to the present invention, the head portion exhibiting a cylindrical distal end.

FIG. 11 shows a head portion 14 exhibiting a distal end 18 or distal tip 35 having a diameter d1. The diameter d1 is in the range of 4.7 mm to 5.2 mm, preferably 4.8 mm to 5 mm, especially 4.9 mm. The distal end 18 has a cylindrical shape. At least one camera 40.1 and/or infrared sensor unit 52; 140 and/or light guide 42 or light source 46 and/or mobility sensor unit 40a is arranged radially offset with a radial offset r1 with respect to a longitudinal axis A of the head portion 14. The camera 40.1 or the respective device has an optical axis X. The camera 40.1 and its optical axis X are tilted against the longitudinal axis A. The tilt angle $\beta$ is e.g. in the range of 10° to 30°. The optical axis X is tilted with respect to a lateral surface of the distal end 18.

The at least one camera 40.1 is arranged at a most distal position, i.e. contacting or providing the distal tip 35. Exemplary, an alternative configuration is shown, the distal tip being provided in a position with a distance A1 (protruding distal tip 35*a*). The distance A1 is a distance between the most distal front side or front surface of the head portion 14, i.e. the protruding distal tip 35*a*, and the most distal (optical) component of the camera 40.1 or the infrared sensor unit 52; 140 or the light source 46. Preferably, each device is positioned at a distance A1 of less than 3 mm, preferably less than 2 mm, more preferable less than 1 mm, from the protruding distal tip 35*a*. This may ensure that a radial offset can provide a most eccentric position of on observation point or illumination point or temperature detection point within the ear canal.

Figure 12:
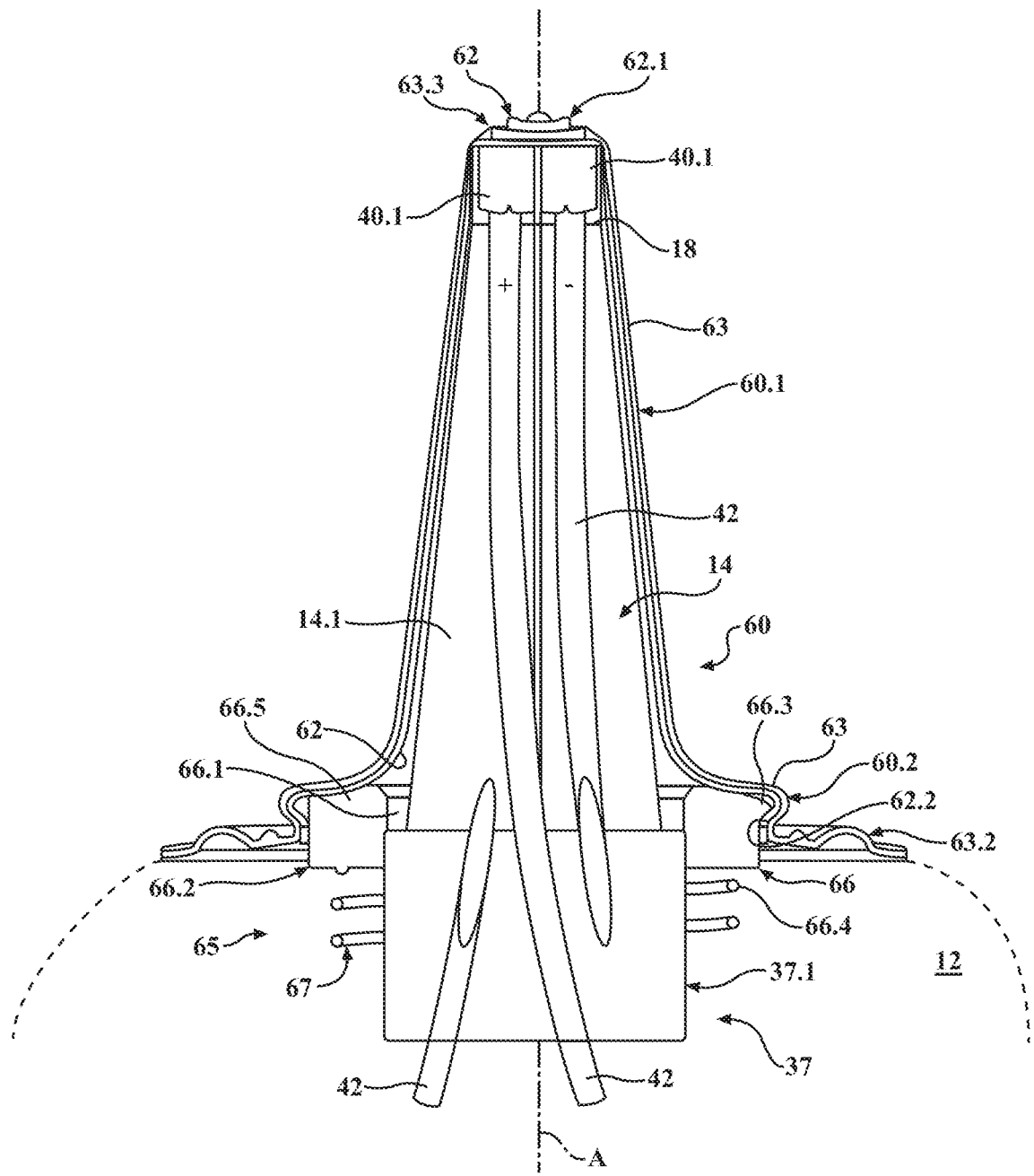
FIG. 12 schematically shows a cross-sectional view of a head portion of a further embodiment of an otoscope according to the present invention, the otoscope comprising a double-ply probe cover which is positioned in a first position.

FIG. 12 shows a head portion 14 of an otoscope, the head portion 14 being connected to a handle portion 12. The head portion 14 exhibits a distal end 18, a conical portion 14.1 and a proximal portion 37. The proximal portion 37 has a cylindrical shape. Within the head portion 14, at least three light guides 42 and cameras 40.1 are arranged. The cameras 40.1 are positioned at the distal end 18 with a radial offset with respect to a longitudinal axis A of the head portion 14. The head portion 14 is covered by a probe cover 60. The probe cover 60 exhibits an inner shell 62 and an outer shell 63. The probe cover 60 is a double-ply probe cover 60, i.e. a double sleeve probe cover. Both shells 62, 63 can be made of a similar material. The shells 62, 63 exhibit a similar shape, which at least partially corresponds to the shape of the head portion 14. In particular, at a distal tip, the inner shell 62 exhibits a distal portion in the form of a compressed or folded portion 62.1 which provides supplemental material of the inner shell 62 at the distal tip. The folded portion 62.1 provides a probe cover reserve. Preferably, the portion 62.1 exhibits concentric circular bends or plaits or folds, in particular a number between 2 and 10, preferably 3 and 8, more preferable 4 and 6, especially 5 bends or folds. It has been found that such a number can ensure an effective unfolding mechanism, wherein the folded portion does not require much space. A probe cover reservoir in the form of concentric circular bends or folds provides the advantage that any groove within the distal end of the head portion for accommodating the probe cover reservoir is not necessarily required. In contrast, the shape of the distal front side of the head portion can be even or plain. This enables accommodating a further sensor, e.g. an infrared sensor, centrically at the distal tip.

At a distal tip, the outer shell 63 exhibits an aperture or opening 63.3. Additionally or as an alternative, at a distal tip, the outer shell 63 can exhibits a predetermined breaking or unfolding point or section 63.4 (as shown in FIG. 7), e.g. a perforation or an incision or an indentation or a notch. In particular, the opening 63.3 can exhibit a circular shape and can have a diameter which is slightly smaller than the diameter of the distal tip of the head portion. Preferably, the diameter of the opening 63.3 is slightly smaller than the diameter of the distal tip by a factor of ⅔ or ½, such that the outer shell 63 is elastically widened or dilated in a radial direction when the probe cover is axially moved with respect to the head portion 14. An opening 63.3 which is smaller than the diameter of the distal tip can ensure that ear wax or any other objects of a patient can be displaced towards the lateral surface of the head portion 14 more effectively.

Preferably, the wall thickness of the probe cover 60 is in a range between 0.05 mm and 0.15 mm, more preferable between 0.07 mm and 0.13 mm, especially about 0.1 mm. The inner shell 62 and the outer shell 63 may exhibit the same wall thickness, at least approximately. As both the inner shell 62 and the outer shell 63 can be produced by deep-drawing, in a distal direction, the wall thickness of both the inner shell 62 and the outer shell 63 may decrease towards the distal end. Preferably, the wall thickness of the folded portion 62.1 is in a range between 0.01 mm and 0.05 mm, more preferable between 0.02 mm and 0.04 mm, especially about 0.02 mm. It has been found that such a wall thickness does not affect the visibility, especially in case the inner shell 62 is made of polypropylene (PP). Preferably, the wall thickness of a conical portion of the inner shell 62 as well as the wall thickness of a conical portion of the outer shell 63 is in a range between 0.02 mm and 0.5 mm, more preferable between 0.02 mm and 0.4 mm, further preferable between 0.02 mm and 0.3 mm.

Preferably, both the inner shell 62 and the outer shell 63 are provided as disposable parts, such that the whole probe cover 60 is a disposable.

Also, it has been found that a relatively low thickness can be realized for each of the shells of the double-ply probe cover 60. Thereby, on the one hand, it is possible to deep-draw each of the shells. On the other hand, the probe cover 60 can be provided with a relatively high stiffness or dimensional stability, as both shells are in close contact with each other and can stabilize each other. Only at the distal tip, there is only one single shell, namely the inner shell, as (according to one alternative) the outer shell exhibits an opening at the distal tip.

Preferably, the inner shell 62 is made of an optically transparent material. The outer shell is not necessarily required to be made of an optically transparent material, as the outer shell exhibits an opening at the distal tip.

Further, the probe cover 60 exhibits a conical portion 60.1 and a groove, rim or undercut 60.2. In particular, this groove 60.2 can be provided by a section of the probe cover 60 which has a sigmoid shape. Preferably, at a proximal end, the inner shell 62 exhibits an U-shaped edge 62.2, and the outer shell 63 exhibits a sigmoid shaped section 63.1 and a radially protruding discoid collar 63.2 (as shown). The collar 63.2 overlaps the handle portion 12 in a radial direction. The collar 63.2 is arranged to partially cover the handle portion 12, especially a cavity in which a probe cover moving mechanism 65 is accommodated, and to protect the handle portion 12 and the moving mechanism 65, e.g. from any body fluids of a patient.

The collar 63.2 is arranged to be fixed at the handle portion 12 and/or at a stationary portion of the head portion 14. Preferably, the collar 63.2 is fixed at the handle portion 12 such that the collar 62.3 is arranged to transmit a torque from the probe cover 60 to the handle portion 12, in order to prevent rotation of the probe cover 60. In other words: Fixing the collar 63.2 is fixed at the handle portion 12 can ensure that the probe cover 60 does not rotate with respect an ear canal when the head portion 14 is rotated within the ear canal, be it manually or by means of a moving mechanism (not shown). Reducing relative motion between the patient's tissue confining the ear canal and the probe cover 60 can prevent irritation of the patient's tissue. In case of rotation, keeping or positioning the probe cover non-moving within the ear canal is preferred. Fixation mechanism may snap in (e.g. by means of three protrusions) into an undercut of the probe cover, but the rotatable portion of the head portion may rotate relative to the snap in fixation.

Preferably, the probe cover 60 is made of polypropylene (PP), especially both the inner shell 62 and the outer shell 63, especially by a thermoforming process, e.g. by means of thin sheets (e.g. 0.38 mm). It has been found that both the inner shell 62 and the outer shell 63 can be produced by deep-drawing. Polypropylene (PP) also provides the advantage of relatively high stiffness. Thereby, it can be ensured that any portions of the probe cover 60 are not displaced until a specific threshold value of an axial force exerted on the probe cover 60 is exceeded. Polypropylene has an elastic modulus of 1.5 GPa-2 GPa, which is relatively stiff. In contrast, polyethylene is more elastic (0.11 GPa-0.45 GPa) and thus less stiff, same as rubber (0.01 GPa-0.1 GPa). As an alternative, the probe cover 60 can be made of polytetrafluoroethylene (PTFE) and can be provided with a porous, gas-permeable structure, at least partially, especially in sections which do not require optical transparency.

The otoscope includes a probe cover moving mechanism 65 which is at least partially arranged between the head portion 14 and the probe cover 60. The moving mechanism 65 includes an adapter 66 and a moving device 67. Preferably, the adapter 66 is connected to the moving device 67 and hold by the moving device 67 in an axial position. Preferably, the adapter 66 is a ring-shaped element exhibiting an inner lateral surface 66.1 and an outer lateral surface 66.2. Preferably, the inner lateral surface 66.1 and the outer lateral surface 66.2 are arranged in parallel to each other. Preferably, the inner lateral surface 66.1 has the same shape as an outer lateral surface 37.1 of the proximal portion 37. In particular, the inner lateral surface 66.1 is arranged to contact the outer lateral surface 37.1 and to slide on the outer lateral surface 37.1. The adapter 66 further exhibits fixing means 66.3, e.g. a kind of collar or radial protrusion or radially protruding edge or rim 66.3, which engages the rim 60.2. In other words: The fixing means 66.3 has a diameter which is bigger than the diameter of the corresponding section of the probe cover 60. Alternatively or in addition, the adapter 66 and/or the probe cover 60 may exhibit a thread for fixing the probe cover 60 at the adapter 66.

The adapter 66 further exhibits a proximal surface, especially a proximal front surface 66.4, which is arranged for transmitting a force in a direction which is at least approximately parallel with the longitudinal axis A. Preferably, the adapter 66 is connected to the moving device 67 and hold by the moving device 67 in an axial position. The adapter 66 further exhibits a distal surface, especially a distal front surface 66.5, which is arranged for transmitting a force in a direction which is at least approximately parallel with the longitudinal axis A. The distal front surface 66.5 is orientated at an angle with respect to the longitudinal axis A which is smaller or bigger than 90°. The distal front surface 66.5 is orientated at an angle with respect to the proximal front surface 66.4 which is preferably in a range between 10° and 50°, more preferable 15° and 30°. The distal front surface 66.5 provides a contact surface for the probe cover 60, especially the inner shell 62. The distal front surface 66.5 corresponds with the probe cover 60, especially with the inner shell 62.

In particular, the moving device 67 can comprise an energy storage, especially in the form of an elastic element. The elastic element preferably is made of metal. The moving device 67 can allow for a mechanical retraction. Preferably, the moving device 67 allows for an axial displacement of about 2 mm. The moving device 67 acts on the front surface 66.4, especially in a direction which is parallel with the longitudinal axis A. For example, the moving device 67 comprises an elastic spring, especially a cylindrical compression spring (as shown), or any alternative elastic element providing the same effect. The moving device 67 shown in FIG. 12 is a mechanical moving device. Optionally, the moving device 67 can be provided as an electric component, e.g. a motor, especially a linear motor. Also, the moving device 67 can be provided as a latch mechanism. In particular, the latch mechanism can exhibit two predefined positions, a first position in which the distal portion (i.e. the probe cover reservoir) of the inner shell is folded, and a first position in which the distal portion of the inner shell is unfolded. These two positions can be defined, e.g., by limit stops or locking devices. The latch mechanism can be coupled to the imaging unit and/or a logic unit. The latch mechanism can be released or actuated manually or automatically. In particular, the latch mechanism can be released in dependence on a signal emitted from the electronic imaging unit, especially a signal which is emitted when (as soon as) the electronic imaging unit is in visual communication with the eardrum. The latch mechanism may comprise an electromagnetic latch which allows to unblock the axial movement upon an electrical signal.

Preferably, in the position shown in FIG. 12, the moving device 67 is not prestressed or elastically preloaded, i.e. the moving device 67 is discharged or relieve of any load. Optionally, the moving device 67 can be preloaded, i.e., the moving device 67 can be supported with a pretension exerted on the probe cover 60. Referring to the position shown in FIG. 12, in case the moving device 67 is arranged for being elastically preloaded, the head portion 14, especially the proximal portion 37, can exhibit a protrusion or a limit stop or locking device (not shown) which ensures that the adapter 66 is not pushed further in the distal direction, but remains in an axial position in which the probe cover 60 can be supported in the first position (as shown) by the adapter 66. Such a pretension can define a threshold value for an axial force which has to be exerted on the adapter 66 in the proximal direction, in order to axially move the probe cover 60 in the proximal direction. Preferably, the moving device 67 is supported by an appropriate supporting structure (not shown) of the head portion 14 or the handle portion 12.

In the following, referring to FIGS. 12 and 13, the functioning of the moving mechanism 65 is explained, especially in conjunction with the double-ply probe cover 60.

First, the probe cover 60 is mounted on the head portion 14, especially in such a way that an inner surface of the probe cover 60 gets in contact with the adapter 66, especially the distal front surface 66.5. Then, the head portion 14 is introduced into the ear canal. As soon as the probe cover 60 gets in contact with an inner lateral surface of the ear canal, a friction force is exerted on the probe cover 60. The friction force depends on the position of the head portion 14 within the ear canal: the friction force increases with increasing insertion depth. The frictional force is directed backwards, i.e. in the direction of the handle portion 12. As the probe cover 60 is in contact with the adapter 66, the frictional force is transmitted to the adapter 66 and to the moving device 67 in the axial direction, at least partially.

As the adapter 66 is axially displaceable or movable, the probe cover 60 can be moved axially with respect to the head portion 14. The compressed or folded portion 62.1 can be unfolded by axial motion of the probe cover 60 with respect to the head portion 14. In other words: The folded portion 62.1 can be unfolded such that only the portion 62.1 (in an unfolded state) of the inner shell 62 covers the distal tip of the head portion 14. The outer shell 63 does not cover the distal tip.

Figure 13:
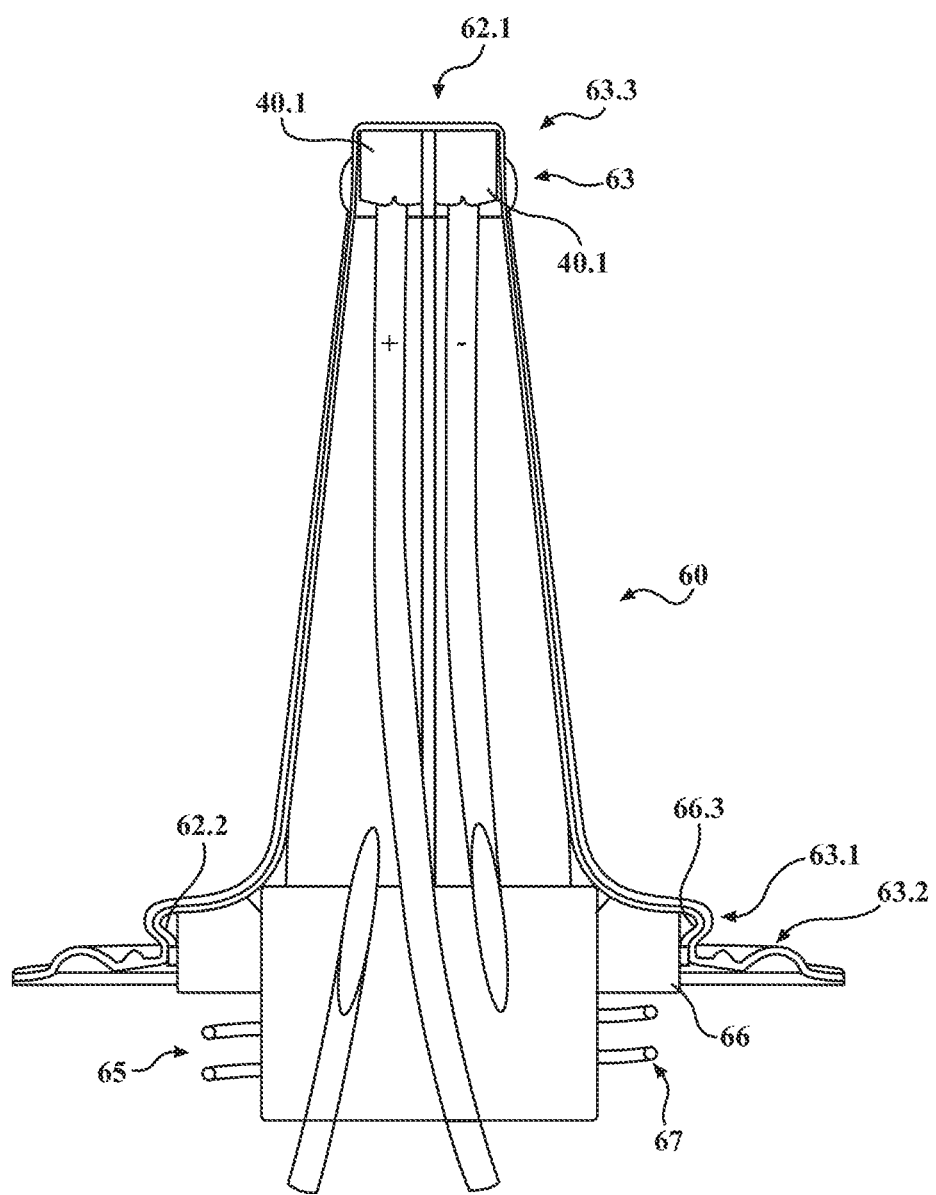
FIG. 13 shows the head portion and the probe cover shown in FIG. 12, the probe cover being positioned in a second position.

FIG. 13 shows the probe cover 60 and the adapter 66 in a second axial position in which the spring 67 is elastically preloaded, i.e. at least partially compressed in the proximal direction. The portion 62.1 of the inner shell 62 closely fits the distal tip of the head portion 14. The portion 62.1 of the inner shell 62 is unfolded and fully in contact with the distal tip. The portion 62.1 covers the distal front side of the head portion and completely lies flat on the distal front side or the distal tip.

In the second position shown in FIG. 13, the cameras 40.1 are not covered by any object other than the inner shell 63. By means of the moving mechanism, the inner shell 63 can be stretched or tensioned. This method step of deploying or unfolding the probe cover 60 can ensure that a field of vision is free of any objects. Any ear wax or any other objects have been pulled away from the distal tip by means of the outer shell 63.

The head portion 14, especially the proximal portion 37, can exhibit a radial protrusion or a limit stop or locking device (not shown) which ensures that the adapter 66 is not pushed further in the proximal direction, but remains in an axial position in which the inner shell 62 is pulled or stretched onto the head portion 14 with a predefined tension. Such a locking device can ensure that the portion 62.1 is not tensioned or stretched more than a predefined threshold value.

As can be seen in FIG. 13, it is not required to provide any groove for accommodating the portion 62.1 of the inner shell 62 at the distal tip of the head portion 14. Nonetheless, the head portion 14 can exhibit a groove or recess arranged for accommodating the portion 62.1 or any other probe cover reserve.

Preferably, the moving mechanism 65 is electrically coupled with at least one of the cameras 40.1 and/or a logic unit. The moving mechanism 65 can exhibit a motion detector (not shown) which is arranged for detecting relative (axial) motion of the probe cover 60 with respect to the head portion 14. In case the probe cover 60 is axially displaced, the motion detector can emit an electric signal which is transmitted to the at least one camera 40.1 or any logical unit or control unit, evoking start-up or powering of the camera 40.1. In such a way, by means of motion detection or detection of the axial position of the probe cover 60, the camera 40.1 can be powered at a time when the camera 40.1 is in visual communication with the eardrum. Thereby, it is possible to reduce an amount of data which has to be processed. Also, the amount of energy required for observing the eardrum can be reduced. Additionally or as an alternative, the moving mechanism 65 can be actuated in dependence on a signal emitted from the camera 40.1, especially a signal which is emitted when (as soon as) the camera 40.1 is in visual communication with the eardrum.

Optionally, the electric signal can be transmitted to one or several light sources (not shown), in order to evoke start-up or powering of the light sources only when the camera 40.1 is in visual communication with the eardrum. Thereby, it is possible to reduce an amount of heat which is emitted by the light sources. Also, the amount of energy required for observing the eardrum can be reduced more effectively.

With the double-ply probe cover 60 shown in FIG. 13, gas (e.g. air) can be passed through one or several cavities arranged between the inner shell 62 and the outer shell 63. This allows for pressurizing the eardrum without any risk of contamination. In particular, the inner shell 62 fully covering the head portion can ensure that any contamination risk is minimized. The gas can be transferred to the distal tip of the probe cover 60. As the outer shell 63 does not (entirely) cover the distal tip, the gas can escape from the cavities and can be passed into the ear canal. There is no need for any porous, gas-permeable section.

Figure 14:
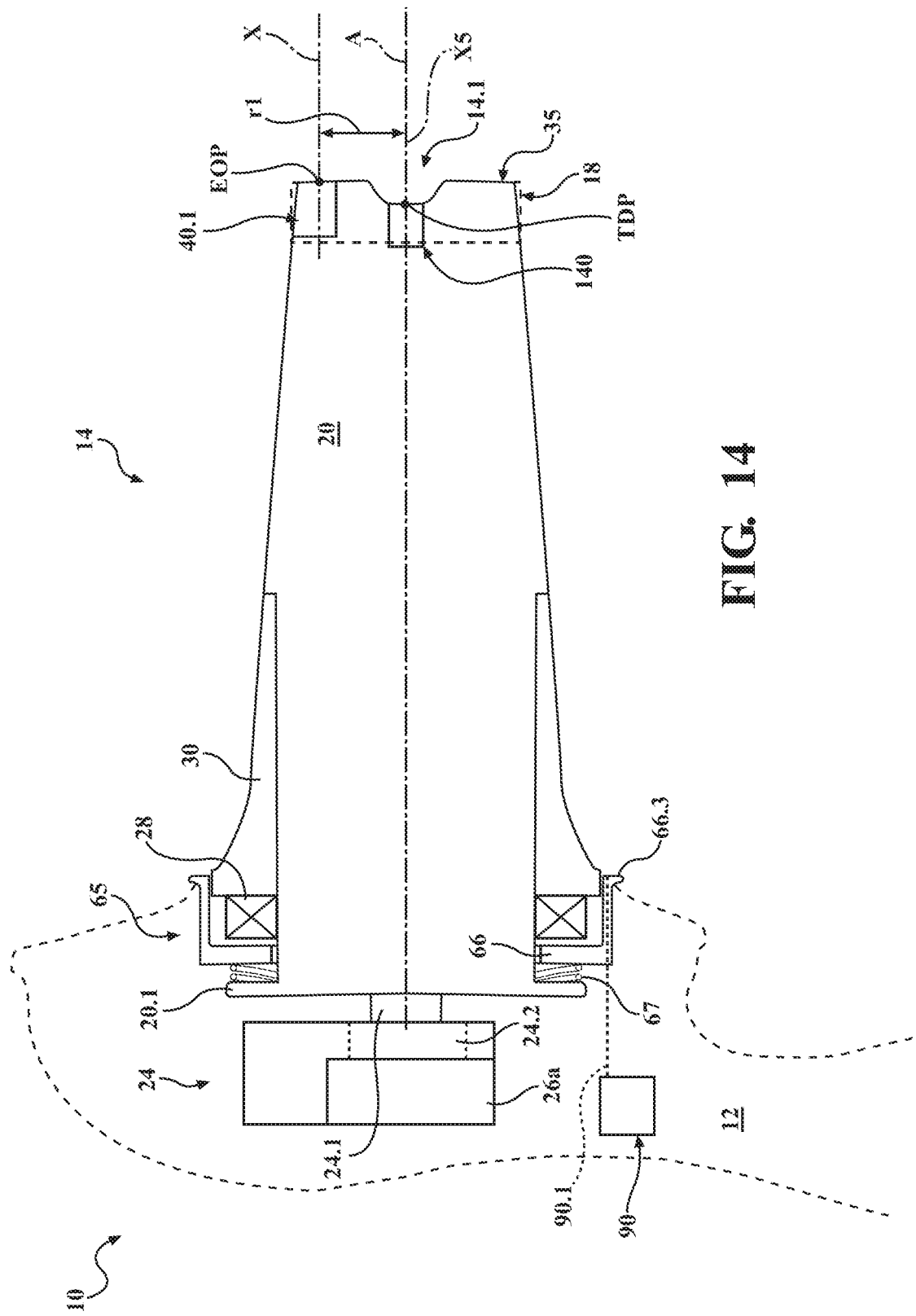
FIG. 14 schematically shows a cross-sectional view of a head portion and of a part of a handle portion of a further embodiment of an otoscope according to the present invention.

FIG. 14 shows an otoscope 10 with a handle portion 12 and a head portion 14. The head portion includes a movable portion 20 and a support structure 30. The movable portion 20 can be rotated by a motion mechanism 24 which is arranged in the handle portion 12. The movable portion 20 can be rotated with respect to the support structure 30. The motion mechanism 24 includes a drive shaft 24.1 which connects the movable portion 20 with the handle portion 12. The motion mechanism 24 includes a brushless motor 26a which is connected to the drive shaft 24.1. Optionally, a gear 24.2 is provided between the motor 26a and the drive shaft 24.1. The movable portion 20 is supported by the bearing 28 which is supported by the handle portion 12. The support structure 30 is supported by the handle portion 12. The support structure 30 provides a portion of the outer lateral surface of the head portion 14. The support structure 30 is fixed at the handle portion 12 by means of the bearing 28.

The head portion 14 has a distal end 18 including a distal tip 35, wherein the distal end 18 has concial shape or a cylindrical shape (as indicated by the dashed line). An infrared sensor unit 140 is positioned centrically at the distal end 18. This position is only illustrated as an example. The infrared sensor unit 140 defines a temperature detection point TDP positioned on the visual axis X5 of the infrared sensor unit 140. The infrared sensor unit 140 shown in FIG. 14 can be provided in conjunction with the other embodiments of the otoscopes as described in the preceding or following figures also. The distal end 18 is provided with an indentation 14.3 for accommodating a portion of a probe cover (not shown). A camera 40.1 having an optical axis X is arranged radially offset with respect to a longitudinal axis A of the head portion 14, wherein the radial offset r1 of the optical axis X preferably is in a range between 1.5 mm and 2 mm. The camera 40.1 defines an eccentric observation point EOP positioned on the optical axis X. Preferably, the eccentric observation point EOP is positioned at the distal tip 35, wherein a distance between the most distal front side or front surface of the head portion 14 and the most distal (optical) component of the electronic imaging unit (i.e., the eccentric observation point EOP) is minimum, preferably zero. The camera 40.1 is positioned adjacent to an inner lateral surface of the distal end 18. Preferably, the camera 40.1 is in contact with the inner lateral surface of the distal end 18.

A probe cover (not shown) can be displaced by a moving mechanism 65, especially axially. Also, the axial position of the probe cover with respect to the head portion 14 can be defined by the moving mechanism 65. The moving mechanism 65 comprises an adapter 66 which exhibits at least one radial protrusion 66.3, especially a collar, which can be coupled with a corresponding contour of a probe cover. The moving mechanism 65 further comprises a moving device 67, especially a compression spring, which is supported by a rim 20.1 of the movable portion 20. An axial force exerted on the probe cover or the head portion 14 in the proximal direction may lead to an axial displacement of the adapter 66 in the proximal direction, especially against a reaction force exerted by the moving device 67. As an alternative, the moving device 67 may be provided in the form of a motor-driven mechanism which can be positioned in predefined axial positions.

The otoscope 10 further exhibits pressurizing means 90 comprising at least one pressure line 90.1 coupling the pressurizing means 90 with the adapter 66. Preferably, the pressure line 90.1 couples the pressurizing means 90, e.g. an air pump, with the radial protrusion or rim 66.3, such that gas can be passed through the adapter 66 or along the adapter 66 and can be passed between a probe cover (not shown) and the head portion 14 or between two shells of a double-ply probe cover (not shown). Preferably, the gas is introduced or outlet at a distal front side or front face of the adapter. In other words: The adapter exhibits a gas conduit which preferably leads to a distal front side or front face of the adapter.

Figure 15:
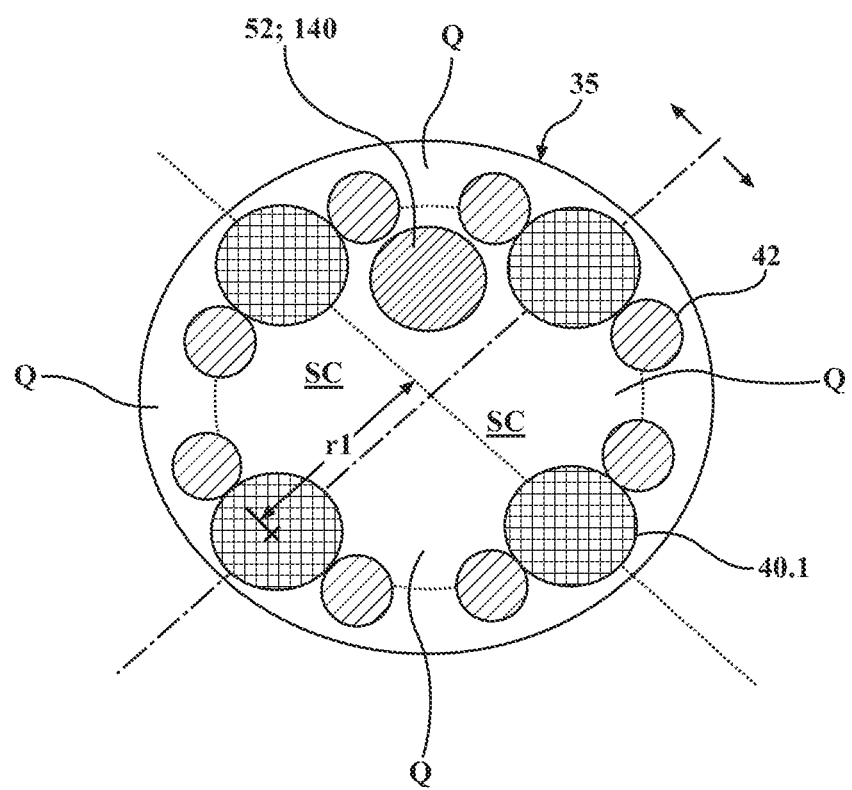
FIG. 15 schematically shows a front view of a distal tip of an otoscope according to the present invention.

FIG. 15 shows a distal tip 35 of an otoscope, wherein four cameras 40.1 are concentrically arranged around a longitudinal axis centrically intersecting the distal tip 35. Each camera 40.1 or an optical axis of each camera 40.1 is positioned at a radial offset r1 from the center of the distal tip 35. Each camera 40.1 is bordered or bounded by two light sources 42. Geometrically, the front face or front side of the distal tip 35 can be sectioned in four quadrants Q, two thereof defining a semicircle SC. Further, an infrared sensor unit 52; 140 is provided at the distal tip 35. The infrared sensor unit 52; 140 is positioned eccentrically. The infrared sensor unit 52; 140 is positioned in the same semicircle SC as one or two of the cameras 40.1. In particular, the infrared sensor unit 52; 140 is positioned in the same quadrant Q as one of the cameras 40.1. This allows for favorably position both the infrared sensor unit 52; 140 and one of the cameras 40.1 in a favorable eccentric position within the ear canal.

Figure 16:
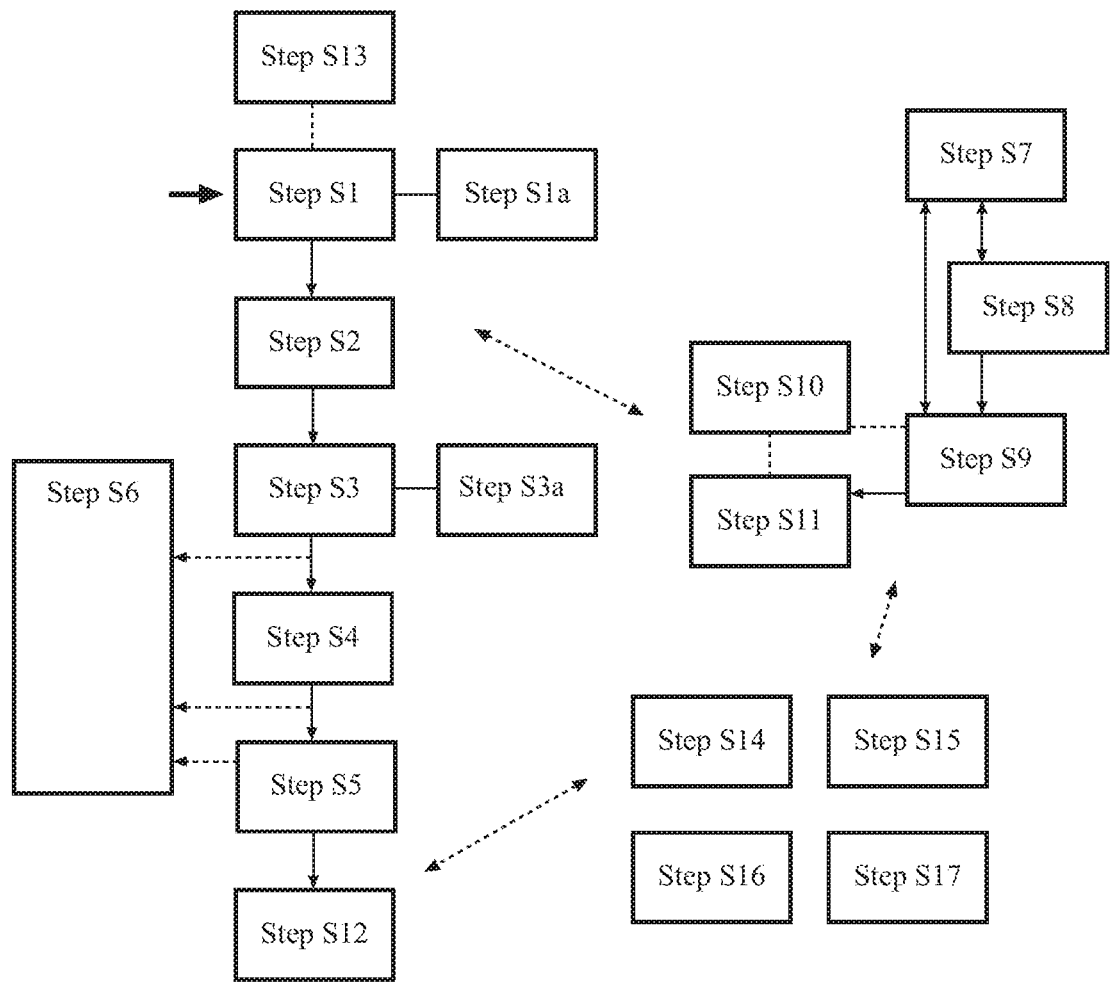
FIG. 16 schematically shows a diagram of steps of a method according to embodiments of the invention.

In FIG. 16, method steps S1 to S17 of methods according to embodiments of the invention as well as interdependencies there between are illustrated. Step S1 comprises introducing the electronic imaging unit. Step S1a comprises introducing the electronic imaging unit in conjunction with an infrared sensor unit. Step S2 comprises capturing at least one image. Step S3 comprises determining brightness and/or color information for identifying objects. Step S3a comprises detecting infrared radiation in conjunction with determining brightness and/or color information for identifying objects. Step S4 comprises comparing images. Step S5 comprises generating a calculated image. Step S6 comprises informing the user that identification of the eardrum has failed.

Step S7 comprises displacing the electronic imaging unit and/or at least one light source. Step S8 comprises tilting the electronic imaging unit or an optical axis thereof, or tilting the light source. Step S9 comprises moving the probe cover with respect to the head portion. Step S10 comprises detecting a force exerted on the probe cover or the head portion. Step S11 comprises motion detection of the probe cover. Step S12 comprises medically characterizing the eardrum. Step S13 comprises user guidance. Step S14 comprises passing a gas through the probe cover. Step S15 comprises calibration. Step S16 comprises segmented lighting. Step S17 comprises temperature measurement by means of an infrared sensor unit.

Methods according to embodiments of the invention start at step S1. Alternatively to step S1, step S1a can be carried out. Alternatively to step S3, step S3a can be carried out. Steps S1 to S6 can be carried out sequentially. Step S6 can be carried out optionally at different steps. Step S12 can be carried out optionally. Step S10 can be carried out independently or in conjunction with e.g. step S9 or S11. Steps S7 to S11 can be carried out in conjunction with each other, and in conjunction with one of steps S1 to S6 or with S12. Steps S7 and S8 can be carried out with respect to a displacement of an (optional) infrared sensor unit also. Step S13 is preferably carried out during step S1 or S1a. Steps S14 to S17 can be carried out in conjunction with each other and/or in conjunction with one of the other steps.

Figure 17:
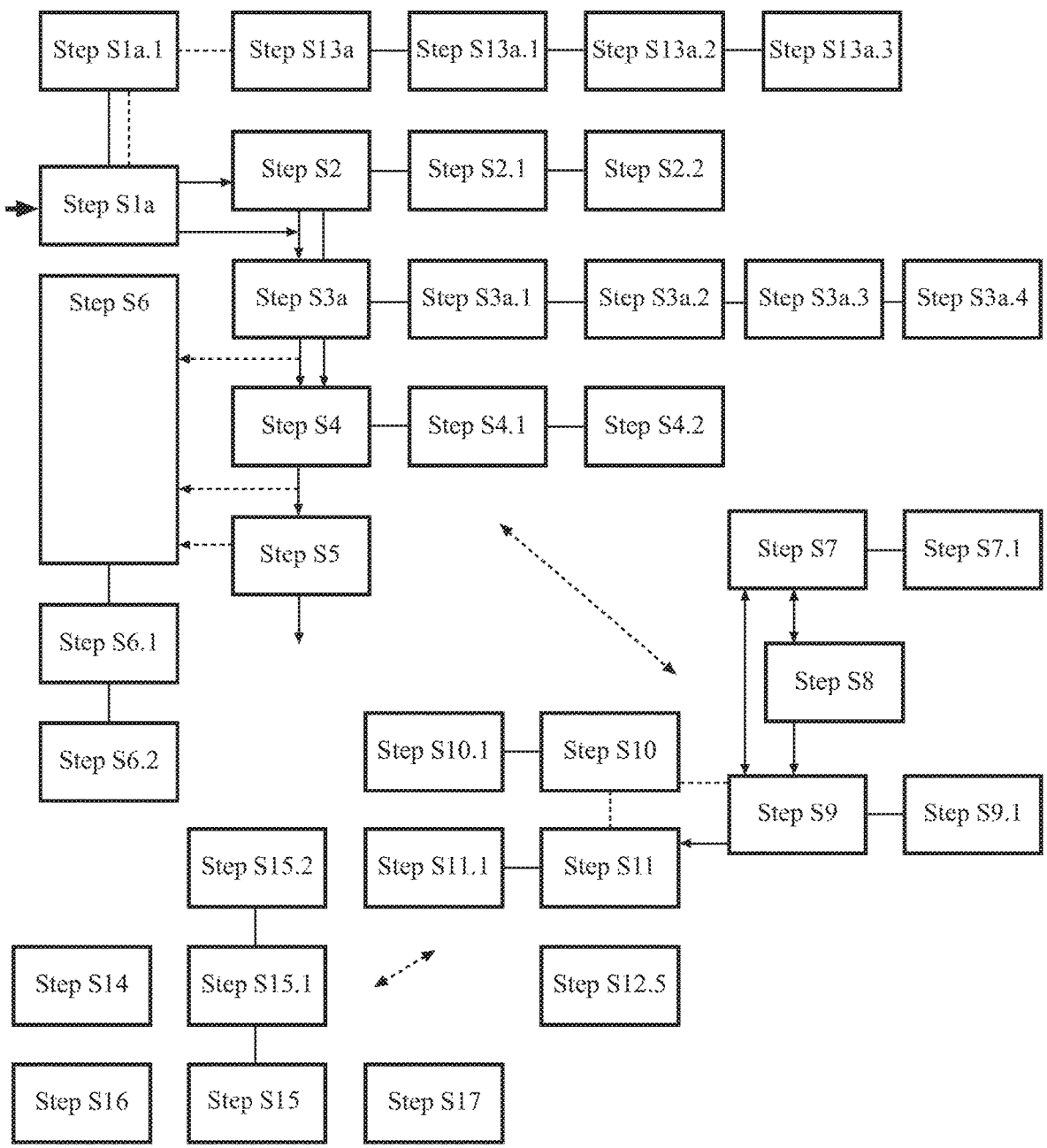
FIG. 17 schematically shows a detailed diagram of steps of a method according to embodiments of the invention.

In FIG. 17, method steps of methods according to embodiments of the invention as well as interdependencies there between are schematically illustrated in detail. In context with steps S1 to S17, it is referred to FIG. 16. In step S1a, also, capturing a plurality of images within a specific time frame can be carried out. At the maximum, e.g., 60 images are captures per second, especially during displacement of the respective optical axis or camera. The step S1a can comprise the step S1a.1 of introducing the electronic imaging unit as well as the infrared sensor unit no further than a predefined distance to the eardrum. The step S2 can comprise the step S2.1 of capturing at least two images from different positions and/or the step S2.2 of capturing at least two images with illumination from different positions. The step S3a can comprise the step S3a.1 of determining the spectral composition of reflections, especially the degree of reddishness, of the eardrum, especially in conjunction with detecting infrared radiation, and/or the step S3a.2 of varying an intensity of illumination, especially in conjunction with detecting infrared radiation, and especially for determining the degree of reddishness, and/or the step S3a.3 of pattern recognition, especially in conjunction with detecting infrared radiation, and especially for identifying the eardrum, and/or the step S3a.4 of determining the distance of objects, especially in conjunction with detecting infrared radiation, and especially for identifying the eardrum. The step S4 can comprise the step S4.1 of discriminating objects by comparing their positions in images captured from different positions and/or the step S4.2 of discriminating objects by comparing their positions in images captured with illumination from different positions. The step S6 can comprise the step S6.1 of informing the user by an acoustic signal and/or the step S6.2 of informing the user by a visual signal.

The steps S1 to S6 relate to capturing images of objects. A method according to the present invention can further comprise at least one of the steps S7 to S11, wherein the steps S7 to S11 are related to a displacement of an optical component of the otoscope and/or a displacement of a probe cover and/or a displacement of an infrared sensor unit. The step S7 can comprise the step S7.1 of rotating the electronic imaging unit an/or at least one light source. The step S9 can comprise the step S9.1 of axially positioning the probe cover. The step S10 can comprise the step S10.1 of activating, especially releasing the moving mechanism in dependence on detected force. The step S11 can comprise the step S11.1 of detecting relative motion of the probe cover by the electronic imaging unit. The step S15 can comprise the step S15.1 of calibrating a spectral sensitivity of the electronic imaging unit and/or the step S15.2 of calibrating color and/or brightness of the at least one light source.

During the step S1, a user guidance can be carried out, in order to position the otoscope more easily within the ear canal, especially with a distal tip arranged in the transition area between soft connective tissue and hard bone, or at the second curvature. A user guidance can be described schematically by a step S13a, the step S13a comprising verifying positioning based on infrared radiation, especially also based on a captured image. The step S13a can further comprise the step S13a.1. The step S13a.1 includes indicating an insertion depth, especially in conjunction with detecting infrared radiation. The step S13a can further comprise the step S13a.2. The step S13a.2 includes indicating a direction of rotation, especially in conjunction with detecting infrared radiation. The step S13a can further comprise the step S13a.3. The step S13a.3 includes indicating a tilting angle of the handle portion, especially in conjunction with detecting infrared radiation. The steps S7, S8, S9, S10 and S11 can be carried out during any of the steps S1a, S13a, S2, S3, S4, S5 and S6.

As shown in FIG. 17, methods according to embodiments of the invention can be carried out without any method step of medically characterizing the eardrum. The method steps shown in FIG. 17 relate to identification of objects.

Figure 18:
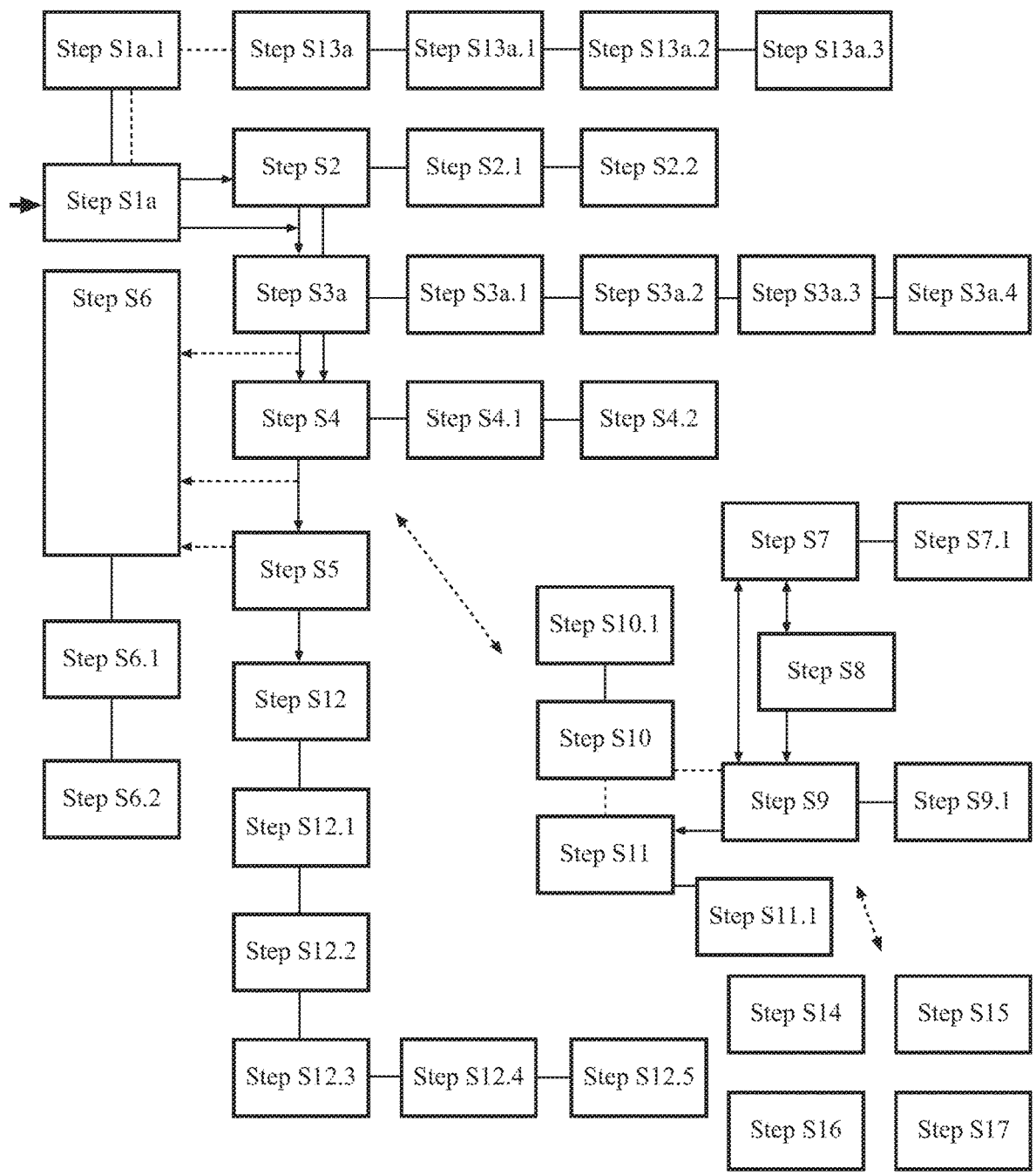
FIG. 18 schematically shows a detailed diagram of steps of a method according to further embodiments of the invention.

In FIG. 18, in addition to the method steps shown in FIG. 17, the methods according to embodiments of the invention include an additional step S12 of medically characterizing the eardrum. The step S12 includes, e.g., providing a suggestion to the user, especially a layperson, as to whether a physician should be visited or not. The step S12 includes, e.g., providing an inflammation index to the user. The step S12 can further comprise the step S12.1. The step S12.1 includes determining the degree of reddishness of the eardrum. The step S12 can further comprise the step S12.2. The step S12.2 includes identifying objects within the tympanic cavity behind the eardrum. The step S12 can further comprise the step S12.3. The step S12.3 includes determining a curvature of the ear drum. The step S12 can further comprise the step S12.4. The step S12.4 includes pressurizing the ear drum. The step S12 can further comprise the step S12.5. The step S12.5 includes determining whether the head portion is positioned within the left or the right ear.

The steps S7, S8, S9, S10, S11 and S12 can be carried out during any of the steps S1a, S13a, S2, S3, S4, S5 and S6 as well as during any of the steps S14 to S17.

Figure 19:
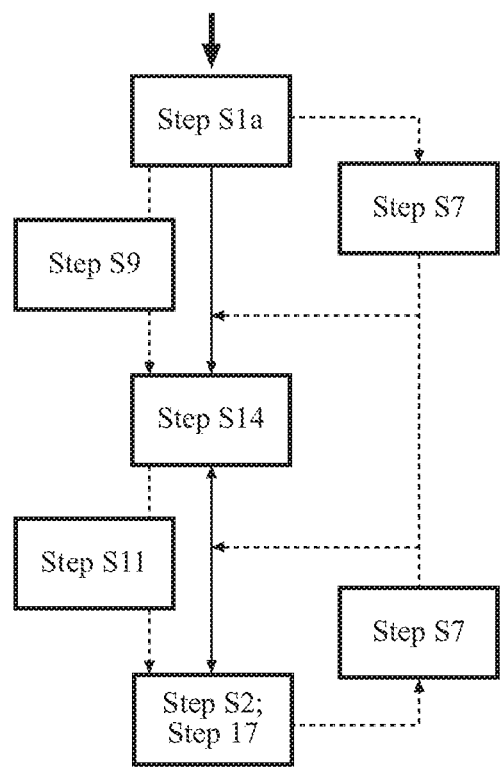
FIG. 19 schematically shows a diagram of steps of a method according to embodiments of the invention.

FIG. 19 shows a diagram of steps S1a, S2, S7, S9, S11, S14 and S17. Step S1a comprises introducing the electronic imaging unit in conjunction with an infrared sensor unit. Step S2 comprises using the electronic imaging unit to capture at least one image from an observation point arranged on the at least one optical axis. Step S7 comprises displacing the electronic imaging unit and/or at least one light source. Step S9 comprises relatively moving at least a portion of the probe cover with respect to at least one optical axis of an optical electronic imaging unit accommodated within the head portion. Preferably, step S9 comprises axially moving a proximal portion of the probe cover and radially moving a distal portion of the probe cover. Step S11 comprises motion detection of the probe cover. S14 comprises passing a gas through a probe cover put over the head portion of the otoscope, especially passing a gas through a double-ply probe cover between two shells of the probe cover. S17 comprises temperature measurement by means of the infrared sensor unit.

Step S9 may be adjusted in dependence on two different scenarios: relatively moving at least a portion of the probe cover can be carried out in dependence on further axial insertion of the head portion (i.e. during insertion of the head portion), or relatively moving at least a portion of the probe cover can be carried out only in case the head portion is arranged at an end position, i.e. the head portion is not introduced any further.

Relatively moving at least a portion of the probe cover in dependence on further axial insertion of the head portion may be favorable with respect to reduced friction between the probe cover and the inner lateral surface of the head portion. Thereby, preferably, the head portion is introduced further, but the relative position of the probe cover with respect to the inner lateral surface of the ear canal remains the same, at least approximately. In other words: friction only occurs between an inner surface of the probe cover and the head portion. Such a relative motion may be assisted by an axial force exerted on the head portion in a distal direction by the user/layperson.

Relatively moving at least a portion of the probe only in case the head portion is arranged at an end position may be favorable with respect to a minimum risk of any artifacts obstructing the view in the ear canal, especially as the distal tip of the head portion is not moved any further with respect to the inner lateral surface. Consequently, its highly improbable that any further ear wax adheres on the distal tip of the probe cover.

Step S7 may be carried out subsequent to step S1a and/or subsequent to S9 or S14 and/or subsequent to S2 or S17. Steps S2 and S17 may be carried out subsequently or simultaneously. Step S11 preferably is carried out prior to step S2 or S17.

The invention claimed is:

1. An ear inspection device configured to be at least partially introduced into a subject's external ear canal for determining a condition of an eardrum in the subject's external ear, wherein the ear inspection device comprises an infrared sensor unit configured to detect infrared radiation from the subject's ear, and wherein the ear inspection device comprises a head portion exhibiting a tapering form extending along a longitudinal axis of the head portion,
    wherein the ear inspection device further comprises an optical electronic imaging unit configured to capture images based on radiation in a visible range from the subject's ear by varying an intensity of illumination provided by at least one light source to identify the eardrum,
    wherein the optical electronic imaging unit is configured to determine a spectral composition of reflections of the eardrum, once the eardrum has been identified,
    wherein the optical electronic imaging unit exhibits at least one optical axis which is arranged so that it is configured to be positioned radially offset within the ear canal, wherein the infrared sensor unit exhibits a visual axis which is positioned centrically within the ear canal or radially offset within a same quadrant, of a cross section of the ear canal, and wherein the radial offset of the at least one optical axis is at least factor 0.25 of a radial dimension of a distal end of the ear inspection device.

2. The ear inspection device according to claim 1 wherein the ear inspection device is configured to position both an eccentric observation point arranged on the at least one optical axis and a temperature detection point arranged on the visual axis most distal within the ear canal with respect to the distal end of the ear inspection device.

3. The ear inspection device according to claim 1 wherein a logic unit is further configured to receive and process signals from the infrared sensor unit and the optical electronic imaging unit, wherein based on the signals, the logic unit is configured to evaluate if the at least one optical axis and/or the visual axis is in visual contact with the eardrum.

4. The ear inspection device according to claim 3 wherein the logic unit is further configured to identify and discriminate different objects in the subject's ear by comparing their appearance in at least two images captured by the optical electronic imaging unit from different eccentric positions within the ear canal or with illumination from different positions within the ear canal.

5. The ear inspection device according to claim 1 wherein the ear inspection device is configured to adjust the intensity of illumination so that a tympanic cavity arranged behind the eardrum is identified.

6. The ear inspection device according to claim 1 wherein the infrared sensor unit comprises a plurality of infrared sensor elements for detecting infrared radiation from different regions of the ear, or wherein the infrared sensor unit is formed by an infrared camera configured to capture images based on radiation in the infrared range from the subject's ear.

7. The ear inspection device according to claim 1 wherein the infrared sensor unit is formed integrally with the optical electronic imaging unit.

8. The ear inspection device according to claim 1 wherein the ear inspection device further comprises a mobility sensor unit configured to detect mobility of the eardrum.

9. The ear inspection device according to claim 1, further comprising pressurization means configured to apply a varying pressure within the subject's external ear canal.

10. The ear inspection device according claim 1 wherein the optical electronic imaging unit comprises at least one color video camera.

11. The ear inspection device according to claim 1, wherein the ear inspection device further comprises:
   a handle portion allowing a user to manipulate the ear inspection device during its application; and
   wherein the head portion has a proximal end adjacent to the handle portion and the distal end configured to be introduced in the subject's external ear canal,
   wherein the optical electronic imaging unit is positioned at the distal end of the head portion, wherein the at least one optical axis is arranged radially offset from the longitudinal axis, and wherein the visual axis is positioned centrically with respect to a distal tip or distal front side of the ear inspection device or is positioned radially offset from the longitudinal axis within the same quadrant of the distal tip about the longitudinal axis.

12. The ear inspection device according to claim 11 wherein the optical electronic imaging unit and/or the infrared sensor unit are positioned at a distance of less than 3 mm from the distal tip.

13. The ear inspection device according to claim 11 wherein the ear inspection device further comprises a motion mechanism configured to allow displacement of the at least one optical axis or of the at least one optical axis and the visual axis relative to the handle portion.

14. The ear inspection device according to claim 13 wherein the motion mechanism is configured to rotate about the at least one optical axis or the infrared sensor unit about an axis of rotation.

15. The ear inspection device according to claim 14 wherein the infrared sensor unit is arranged so as to maintain a predetermined distance with respect to the optical electronic imaging unit or at least one optical axis when the at least one optical axis is displaced by the motion mechanism.

16. A method of determining a condition of a subject's ear, wherein the method comprises:
   introducing an ear inspection device of claim 1, at least partially into the subject's external ear canal, the ear inspection device comprising an infrared sensor unit and an optical electronic imaging unit, wherein the optical electronic imaging unit exhibits at least one optical axis, and wherein the ear inspection device comprises a head portion exhibiting a tapering form extending along a longitudinal axis of the head portion;
   detecting infrared radiation from the subject's ear using the infrared sensor unit, wherein the infrared sensor unit exhibits a visual axis;
   capturing at least one image based on radiation in a visible range from the subject's ear using the electronic imaging unit, wherein capturing at least one image is carried out from at least one eccentric observation point positioned on the at least one optical axis eccentrically within the ear canal, and wherein detecting infrared radiation is carried out from a temperature detection point positioned on the visual axis and positioned centrically within the ear canal or positioned eccentrically within the ear canal or radially offset within a same quadrant, of a cross section of the ear canal, and wherein the radial offset of the at least one optical axis is at least factor 0.25 of a radial dimension of a distal end of the ear inspection device;
   medically characterizing an eardrum of the subject's ear based on the detected infrared radiation and on at least one captured image, wherein medically characterizing the eardrum includes determining a degree of reddishness of the eardrum or identifying objects within a tympanic cavity of the subject; and
   determining a condition of the subject's ear based on the medical characterization of the eardrum.

17. The method according to claim 16, further comprising at least one of the following steps:
   verifying appropriate positioning of the ear inspection device with respect to the subject's ear based on the detected infrared radiation and/or the at least one captured image;
   determining whether the ear inspection device is positioned within a left or a right ear of the subject based on the at least one captured image; and
   discriminating different objects in the subject's ear, by comparing their appearance in at least two images captured by the optical electronic imaging unit from different eccentric positions within an ear canal and/or with illumination from different positions within the ear canal.

18. The method according to claim 16, wherein medically characterizing the eardrum further includes determining a curvature of the eardrum and/or detecting mobility of the eardrum during pressurizing the eardrum.

19. The method according to claim 16, further comprising providing a user with information indicating a likelihood of a specific disease.

20. The method according to claim 16, wherein identifying objects within the tympanic cavity comprises transilluminating the eardrum and capturing at least one image of light reflected from the tympanic cavity in order to obtain information about the tympanic cavity.

21. A method of determining temperature of a subject's eardrum and medically characterizing the eardrum, wherein the method comprises:
   introducing an ear inspection device, according to claim 1, at least partially into the subject's external ear canal, the ear inspection device comprising an infrared sensor unit and an optical electronic imaging unit, wherein the optical electronic imaging unit exhibits at least one optical axis, and wherein the ear inspection device comprises a head portion exhibiting a tapering form extending along a longitudinal axis of the head portion;
   detecting infrared radiation from the eardrum using the infrared sensor unit, wherein the infrared sensor unit exhibits a visual axis; and
   capturing at least one image based on radiation in a visible range from the eardrum using the electronic imaging unit,
   wherein capturing at least one image is carried out from at least one eccentric observation point positioned on the at least one optical axis eccentrically within the ear canal, and wherein detecting infrared radiation is carried out from a temperature detection point positioned on the visual axis and positioned centrically within the ear canal or radially offset within a same quadrant of a cross section of the ear canal medically characterizing the eardrum based on determining color information or brightness and color information in the at least one image of the eardrum by a logic unit, wherein medically characterizing the eardrum includes determining a degree of reddishness of the eardrum or identifying objects within a tympanic cavity of the subject, and wherein the radial offset of the at least one optical axis is at least factor 0.25 of a radial dimension of a distal end of the ear inspection device; and determining a condition of the subject's ear based on the medical characterization of the eardrum.

22. The ear inspection device according to claim 1, wherein the condition of the subject's ear is temperature.

23. The ear inspection device according to claim 4, wherein the different objects in the subject's ear include earwax, hair, or the eardrum.

24. The ear inspection device according to claim 5, wherein the ear inspection device is configured to adjust the intensity of illumination so that light emitted by the at least one light source at least partially transilluminates the eardrum and is reflected by any object or fluid within the tympanic cavity.

25. The ear inspection device according to claim 11, wherein the optical electronic imaging unit is positioned at the distal tip.

26. The ear inspection device according to claim 1, wherein the radial offset of the at least one optical axis is at least factor 0.3 of the radial dimension of the distal end.

27. The ear inspection device according to claim 26, wherein the radial offset of the at least one optical axis is at least factor 0.35 of the radial dimension of the distal end.

28. The ear inspection device according to claim 12, wherein the optical electronic imaging unit and/or the infrared sensor unit are positioned at a distance of less than 2 mm from the distal tip.

29. The ear inspection device according to claim 28, wherein the optical electronic imaging unit and/or the infrared sensor unit are positioned at a distance of less than 1 mm from the distal tip.

30. The ear inspection device according to claim 14, wherein the axis of rotation is the longitudinal axis.

31. The method according to claim 16, wherein the condition of the subject's ear is temperature.

32. The method according to claim 16, wherein detecting infrared radiation is carried out from a temperature detection point positioned eccentrically within the ear canal within a same quadrant of the cross section of the ear canal.

33. The method according to claim 17, wherein the different objects are earwax, hair, and the eardrum.

34. The method according to claim 17, wherein the illumination is from different eccentric positions within the ear canal.

35. The method according to claim 16, wherein medically characterizing the eardrum includes determining a convexity of the eardrum.

36. The method according to claim 19, further comprising providing a user with information indicating a likelihood of otitis media.

37. The ear inspection device according to claim 1, wherein the optical electronic imaging unit is configured to determine a degree of reddishness of the eardrum, once the eardrum has been identified.

38. The ear inspection device according to claim 1, wherein the ear inspection device further comprises a logic unit configured to medically characterize the eardrum based on determining color information or brightness and color information in at least one image of the images of the eardrum and determine a condition of the subject's ear based on the medical characterization, wherein medically characterizing the eardrum includes determining a degree of reddishness of the eardrum or identifying objects within a tympanic cavity of the subject.

39. The ear inspection device according to claim 1, wherein the ear inspection device is configured to vary the intensity of illumination to at least a first intensity based on a first area of interest of the eardrum and second intensity based on a second area of interest of the eardrum different than the first area of interest.

* * * * *